United States Patent [19]
Kitano et al.

[11] Patent Number: 5,789,448
[45] Date of Patent: Aug. 4, 1998

[54] BENZOYLETHYLENE DERIVATIVE

[75] Inventors: Yasunori Kitano; Haruki Inokawa; Hisao Takayanagi, all of Kanagawa; Tamaki Yano, Tokyo; Hiroe Umeki; Hiroto Hara, both of Kanagawa, all of Japan

[73] Assignee: Mitsubishi Chemical Corporation, Tokyo, Japan

[21] Appl. No.: 619,519

[22] PCT Filed: Jul. 25, 1995

[86] PCT No.: PCT/JP95/01475

§ 371 Date: Jun. 25, 1996

§ 102(e) Date: Jun. 25, 1996

[87] PCT Pub. No.: WO96/03364

PCT Pub. Date: Feb. 8, 1996

[30] Foreign Application Priority Data

Jul. 27, 1994 [JP] Japan .................................. 6-175357

[51] Int. Cl.⁶ .................. A61K 31/165; C07C 235/76
[52] U.S. Cl. .................. 514/649; 514/445; 514/523; 549/66; 558/401; 564/340; 564/342; 564/344; 564/345
[58] Field of Search .................. 564/340, 342, 564/344, 345; 558/401; 514/523, 649, 445; 549/66

[56] References Cited

U.S. PATENT DOCUMENTS

| | | | |
|---|---|---|---|
| 3,864,344 | 2/1975 | Raabe et al. | 544/400 |
| 4,418,079 | 11/1983 | Kojima et al. | 514/649 |

FOREIGN PATENT DOCUMENTS

| | | |
|---|---|---|
| 201121 | 2/1980 | Czechoslovakia . |
| 0 537 742 A2 | 10/1992 | European Pat. Off. . |
| 0 608 897 A2 | 1/1994 | European Pat. Off. . |
| 0 645 379 A2 | 7/1994 | European Pat. Off. . |
| 63-130564 | 6/1988 | Japan . |

OTHER PUBLICATIONS

European Journal of Med. Chem., vol. 23(1), pp. 45–52, (1988), Mario Bianchi, et al., "Gastric Anti–Secretory, Anti–Ulcer and Cytoprotective Properties of Substituted (E)–4–Phenyl– and Heteroaryl–4–Oxo–2–Butenoic Acids".

Collection of Czechoslovak Chemical Communications, vol. 28, pp. 3278–3289, (1963), M. Semonský, et al., "Substanzen mit Antineoplastischer Wirksamkeit VI. Aminolyse Von γ–Aryl–α,β–Dihalogen–Δ$^{α,β}$–Crotonlactonen; Einige Substituierte β–Aroyl–β–Halogen Acrylsäureamide und –Propionsäureamide Sowie β–Aroylpropionsäureamide".

Collection of Czechoslovak Chemical Communications, vol. 41, pp. 3106–3112, (1976), V. Zikán, et al., "Synthesis and Saponification of Ethyl Esters of cis– and trans–β–4–Alkoxybenzoyl–β– and –β–Bromoacrylic Acids".

Journal of the Chemical Society, vol. (B), pp. 156–160, (1971), K. Bowden, et al., "Reactions of Carbonyl Compounds in Basic Solutions. Part IV. The Mechanism of the Alkaline Hydrolysis of Methyl 3–Benzoylacrylates".

Journal of the Chemical Society, Perkin Transactions, vol. 1, pp. 2721–2728, (1990), Donald J. Coveney, et al., "Acylocobalt Salophen Reagents. Precursors to Acyl Radical Intermediates for Use in Carbon–To–Carbon Bond–Forming Reactions to Alkenes".

Journal of American Chemical Society, vol. 110, pp. 1557–1565, (1988), Antonio M. Echavarren, et al., "Palladium–Catalyzed Carbonylative Coupling of Aryl Triflates with Organostannanes".

Journal of the Chemical Society, Perkin Transactions I, pp. 1588–1594, (1978), John W. Apsimon, et al., "Synthesis of Some 2–Phenylpyrrole Derivatives".

Journal of Organic Chemistry of the USSR, vol. 8, No. 4, pp. 735–738, (1972), I.G. Tishchenko, et al., "Liquid–Phase Oxidation of α,β–Unsaturated Ketones. X. Oxidation of Alkoxyisobutylidebeacetophenoes".

*Primary Examiner*—Richard L. Raymond
*Attorney, Agent, or Firm*—Oblon, Spivak, McClelland, Maier & Neustadt, P.C.

[57] ABSTRACT

Disclosed is a benzoylethylene derivative represented by the following formula (I) or a salt thereof.

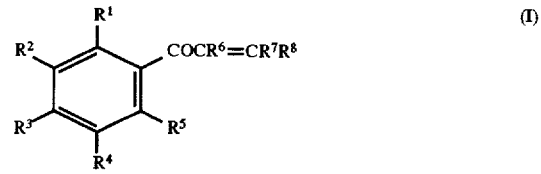

$R^1$ to $R^5$: a hydrogen atom, —$OR^9$ ($R^9$: a hydrogen atom, a $C_1$–$C_5$ alkyl group, etc.), etc., $R^6$: a hydrogen atom, a $C_1$–$C_5$ alkyl group, etc., $R^7$: a hydrogen atom, a cyano group, a $C_1$–$C_5$ alkyl group, —$SO_qR^{15}$ (q: 0, 1, 2, $R^{15}$: a thienyl group, a phenyl group, etc.) etc., $R^8$: a cyano group, —$CR^{22}R^{23}X$ ($R^{22}$, $R^{23}$: a hydrogen atom, a $C_1$–$C_5$ alkyl group, etc., X: —$NR^{24}R^{25}$ ($R^{24}$, $R^{25}$: a $C_1$–$C_5$ alkyl group, etc., an alkylene group by combining, etc.)), etc.

The benzoylethylene derivative of the present invention has potent tyrosine kinase inhibiting activity and cancer cell growth inhibiting activity. The tyrosine kinase inhibitor of the present invention is useful as a carcinostatic agent.

7 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Arg Arg Leu Ile Glu Asp Ala Glu Tyr Ala Ala Arg Gly
 1           5                   10
```

BENZOYLETHYLENE DERIVATIVE

The present application is a 371 application of PCT/JP95/01475, filed Jul. 25, 1995.

TECHNICAL FIELD

This invention relates to a tyrosine kinase inhibitor, more specifically to a tyrosine kinase inhibitor containing a benzoylethylene derivative having specific structure or a pharmaceutically acceptable salt thereof as an active ingredient.

BACKGROUND ART

In chemotherapy of cancer, many substances have been practically used as a medicine. In many cases, however, they are not necessarily in a satisfactory situation since not only the effect of the substance as a medicine is insufficient but also the inhibitory activity thereof is not limited only to cancer cells and the substance shows potent toxicity so that side effects thereof are a great problem.

It has been known that a receptor of a growth factor controls function of differentiation and growth of cells and when a kind of aberration occurs, abnormal growth (excrescence) and differentiation of cells occur and the cells become cancerous. It has been clarified that tyrosine kinase type acceptors participate particularly in formation of cancer, and found that these acceptors show peculiar tyrosine-specific protein kinase (tyrosine kinase) activities and these activities are particularly accelerated in cancer cells (Cancer Research, 51, 4430–4435 (1991); Cancer Research, 52, 3636–3641 (1992); Cancer Chemother. Pharmacol., 32, 1–19 (1993), etc.). Based on these findings, it has been already proposed that an agent which specifically inhibits tyrosine kinase activity of a growth factor acceptor become to be a carcinostatic agent having novel function and mechanism with less side effect. In such a material, there are, for example, microorganism-derived Erbstatin, Lavendustin, Herbimycin A, Genistein, etc., and as chemically synthesized products, benzylidene malonic nitrile derivative [Japanese Provisional Patent Publication No. 138238/1990; Journal of Medicinal Chemistry, 32, 2344 (1989); Ditto, 34, 1896 (1991)], α-cyanocinnamide derivative (Japanese Provisional Patent Publication No. 222153/1988), 3,5-diisopropyl-4-hydroxystyrene derivative (Japanese Provisional Patent Publication No. 39522/1987), 3,5-di-t-butyl-4-hydroxystyrene derivative (Japanese Provisional Patent Publication No. 39523/1987), Erbstatin derivative compound (Japanese Provisional Patent Publication No. 277347/1987), and the like.

The conventional tyrosine kinase inhibitors are each insufficient in their inhibitory activities and they are not yet sufficient for using as a carcinostatic agent. An object of the present invention is to provide a novel compound useful as a carcinostatic agent which can be easily available, has high activity specifically as a tyrosine kinase inhibitor of a growth factor acceptor, and thus has no side effects which are possessed by the conventional carcinostatic agents. Also, it has been well known that tyrosine-specific protein kinase (tyrosine kinase) has central function in differentiation and growth of cells or in cell information transfer mechanism, and failure in control of tyrosine kinase activity in cells causes aberration in differentiation and growth mechanism of cells or in cell information transfer mechanism which is considered to directly participate in crisis of many diseases. For example, these diseases are arteriosclerosis (Am. J. Physiol., 260 (4-part 1), C721–C730 (1991); Biochem. Biophys. Res. Commun., 192 (3), 1319–1326 (1993), etc.), platelet aggregation (FEBS Letters, 263 (1), 104–108 (1990); FEBS Letters, 309 (1), 10–14 (1992), etc.), immune disorder (FEBS Letters, 279 (2), 319–322 (1991); J. Immunol., 146 (9), 2965–2971 (1991); Nature, 358, 253–255 (1992), etc.), inflammation (Molecular Pharmacology, 37, 519–525 (1990); International Immunology, a (4), 447–453 (1992), etc.) or the like. Thus, tyrosine kinase inhibitors are considered to be useful for treatment and prevention of these diseases.

DISCLOSURE OF THE INVENTION

The present inventors have intensively studied to solve the above problems and as a result, they have found that a benzoylethylene derivative with specific structure has potent tyrosine kinase inhibiting activity and cancer cell growth inhibiting activity nothing beyond this whereby they have accomplished the present invention. That is, the summary of the present invention resides in a benzoylethylene derivative represented by the following formula (I):

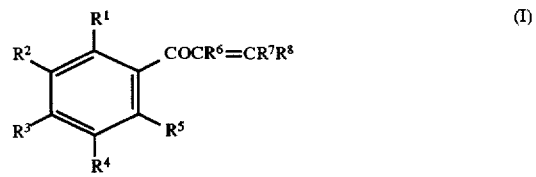

[wherein, in the above formula (I), $R^1$ to $R^5$ each independently represent (1) a hydrogen atom, (2) —$OR^9$ [wherein $R^9$ represents a hydrogen atom or a $C_1$–$C_5$ alkyl group which may be substituted by a halogen atom or a phenyl group.], (3) a halogen atom, (4) a $C_1$–$C_5$ alkyl group which may be substituted by a halogen atom, (5) —$NR^{10}R^{11}$ (wherein $R^{10}$ and $R^{11}$ each independently represent a hydrogen atom, a phenyl group, a $C_1$–$C_5$ alkyl group which may be substituted by a phenyl group, a benzoyl group or an acetyl group.), (6) —$SO_pR^{12}$ (wherein p represents 0, 1 or 2, and $R^{12}$ represents a $C_1$–$C_5$ alkyl group or a phenyl group.), (7) a cyano group or (8) a nitro group, or represent a $C_1$–$C_3$ oxyalkylene group having 1 or 2 oxygen atoms by combining the adjacent substituents.

$R^6$ and $R^7$ each independently represent (1) a hydrogen atom, (2) a cyano group, (3) a halogen atom, (4) a $C_1$–$C_5$ alkyl group which may be substituted by a halogen atom, (5) —$NR^{13}R^{14}$ (wherein $R^{13}$ and $R^{14}$ each independently represent a hydrogen atom or a $C_1$–$C_5$ alkyl group, or are combined together to form a $C_3$–$C_6$ alkylene group which may be intervened by —O—.) or (6) —$SO_qR^{15}$ (wherein q represents 0, 1 or 2, and $R^{15}$ represents a $C_1$–$C_5$ alkyl group which may be substituted by a halogen atom, a thienyl group or a phenyl group which may be substituted by a halogen atom, a $C_1$–$C_5$ alkyl group, a cyano group, a nitro group or a $C_1$–$C_5$ alkoxy group.).

$R^8$ represents (1) a cyano group, (2) —$COR^{16}$ [wherein $R^{16}$ represents a $C_1$–$C_5$ alkoxy group which may be substituted by a phenyl group, or —$NR^{17}R^{18}$ (wherein $R^{17}$ and $R^{18}$ each independently represent a hydrogen atom or a phenyl group which may be substituted by a halogen atom or a $C_1$–$C_5$ alkyl group.).] or (3) —$CR^{22}R^{23}X$ {wherein $R^{22}$ and $R^{23}$ each independently represent a hydrogen atom or a $C_1$–$C_5$ alkyl group, or are combined together to represent a $C_3$–$C_6$ alkylene group which may be substituted by a $C_1$–$C_5$ alkyl group, and X represents a hydroxyl group or —$NR^{24}R^{25}$ [wherein $R^{24}$ and $R^{25}$ each independently represent (a) a hydrogen atom, (b) a phenyl group which may be substituted by a halogen atom or a $C_1$–$C_5$ alkyl group, (c) a $C_1$–$C_5$ alkyl group which may be substituted by a phenyl group or a $C_1$-$C_5$ alkylamino group, (d) a $C_3$-$C_8$ cycloalkyl group or (e) —$COR^{26}$ (wherein $R^{26}$ represents a $C_1$-$C_5$ alkyl group, a phenyl group or a $C_1$-$C_5$ alkoxy group which may be substituted by a phenyl group.), or are combined together to represent a $C_3$-$C_6$ alkylene group which may be intervened by —O— or —$NR^{27}$— (wherein $R^{27}$ represents a hydrogen atom or a $C_1$-$C_5$ alkyl group.), or a $C_3$-$C_6$ alkylene group which may be substituted by a $C_1$-$C_5$ alkyl group.].}. Provided that when $R^6$ and $R^7$ represent hydrogen atoms simultaneously, $R^{16}$ does not represent —$NR^{17}R^{18}$.] or a salt thereof, or a tyrosine kinase inhibitor containing the above benzoylethylene derivative or a salt thereof as an active ingredient.

In the following, the present invention is explained in detail.

The tyrosine kinase inhibitor of the present invention contains the benzoylethylene derivative represented by the above formula (I) or a pharmaceutically acceptable salt thereof as an active ingredient. As the halogen atom defined in the formula (I), there may be mentioned, a fluorine atom, a chlorine atom, a bromine atom, an iodine atom, etc., as the $C_1$-$C_5$ alkyl group, there may be mentioned a methyl group, an ethyl group, a n-propyl group, an iso-propyl group, a n-butyl group, an iso-butyl group, a sec-butyl group, a tert-butyl group, a n-pentyl group, a neopentyl group, etc., and as the $C_1$-$C_5$ alkoxy group, there may be mentioned a methoxy group, an ethoxy group, a n-propoxy group, an iso-propoxy group, a n-butoxy group, an iso-butoxy group, a sec-butoxy group, a tert-butoxy group, a n-pentyloxy group, a neopentyloxy group, etc.

As the $C_3$-$C_8$ cycloalkyl group, there may be mentioned a cyclopropyl group, a cyclobutyl group, a cyclopentyl group, a cyclohexyl group, a cycloheptyl group and a cyclooctyl group, and as the $C_1$-$C_5$ alkylamino group, there may be mentioned a methylamino group, an ethylamino group, a n-propylamino group, an iso-propylamino group, a n-butylamino group, a tert-butylamino group, a n-pentylamino group, etc.

As the $C_1$-$C_3$ oxyalkylene group having 1 or 2 oxygen atoms, there may be mentioned —$OCH_2CH_2$—, —$CH_2OCH_2$—, —$CH_2CH_2O$—, —$OCH_2O$—, —$OCH_2CH_2O$—, etc., and as the $C_3$-$C_6$ alkylene group, there may be mentioned —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—.

Among the compounds represented by the above formula (I), preferred are compounds in which $R^8$ is a cyano group or —$CR^{22}R^{23}X$ {wherein $R^{22}$ and $R^{23}$ each independently represent a hydrogen atom or a $C_1$-$C_5$ alkyl group, or are combined together to represent a $C_3$-$C_6$ alkylene group which may be substituted by a $C_1$-$C_5$ alkyl group, and X represents a hydroxyl group or —$NR^{24}R^{25}$ [wherein $R^{24}$ and $R^{25}$ each independently represent (a) a hydrogen atom, (b) a phenyl group which may be substituted by a halogen atom or a $C_1$-$C_5$ alkyl group, (c) a $C_1$-$C_5$ alkyl group which may be substituted by a phenyl group or a $C_1$-$C_5$ alkylamino group, (d) a $C_3$-$C_8$ cycloalkyl group or (e) —$COR^{26}$ (wherein $R^{26}$ represents a $C_1$-$C_5$ alkyl group, a phenyl group or a $C_1$-$C_5$ alkoxy group which may be substituted by a phenyl group.), or are combined together to represent a $C_3$-$C_6$ alkylene group which may be intervened by —O— or —$NR^{27}$— (wherein $R^{27}$ represents a hydrogen atom or a $C_1$-$C_5$ alkyl group.), or a $C_3$-$C_6$ alkylene group which may be substituted by a $C_1$-$C_5$ alkyl group.].}. More preferred are compounds in which $R^7$ is a hydrogen atom, a cyano group, a $C_1$-$C_5$ alkyl group or —$SO_qR^{15}$ (wherein q represents 0, 1 or 2, and $R^{15}$ represents a $C_1$-$C_5$ alkyl group which may be substituted by a halogen atom, a thienyl group or a phenyl group which may be substituted by a halogen atom, a $C_1$-$C_5$ alkyl group, a cyano group, a nitro group or a $C_1$-$C_5$ alkoxy group.), and $R^8$ is a cyano group or —$CR^{22}R^{23}X$ {wherein $R^{22}$ and $R^{23}$ each independently represent a hydrogen atom or a $C_1$-$C_5$ alkyl group, or are combined together to represent a $C_3$-$C_6$ alkylene group which may be substituted by a $C_1$-$C_5$ alkyl group, and X represents a hydroxyl group or —$NR^{24}R^{25}$ [wherein $R^{24}$ and $R^{25}$ each independently represent (a) a hydrogen atom, (b) a phenyl group which may be substituted by a halogen atom or a $C_1$-$C_5$ alkyl group, (c) a $C_1$-$C_5$ alkyl group which may be substituted by a phenyl group or a $C_1$-$C_5$ alkylamino group, (d) a $C_3$-$C_8$ cycloalkyl group or (e) —$COR^{26}$ (wherein $R^{26}$ represents a $C_1$-$C_5$ alkyl group, a phenyl group or a $C_1$-$C_5$ alkoxy group which may be substituted by a phenyl group.), or are combined together to represent a $C_3$-$C_6$ alkylene group which may be intervened by —O— or —$NR^{27}$— (wherein $R^{27}$ represents a hydrogen atom or a $C_1$-$C_5$ alkyl group.), or a $C_3$-$C_6$ alkylene group which may be substituted by a $C_1$-$C_5$ alkyl group.].}.

Further, as a particularly preferred compound, there may be mentioned compounds in which $R^1$ and $R^5$ are hydrogen atoms, $R^2$, $R^3$ and $R^4$ each independently are a hydrogen atom or —$OR^{9'}$ (wherein $R^{9'}$ represents a $C_1$-$C_5$ alkyl group.), or $R^2$ and $R^3$ are combined to be $C_1$-$C_3$ oxyalkylene having 1 or 2 oxygen atoms, $R^6$ is a hydrogen atom or a $C_1$-$C_5$ alkyl group, $R^7$ is a hydrogen atom, a cyano group, a $C_1$-$C_5$ alkyl group or —$SO_qR^{15'}$ (wherein q' represents 2, and $R^{15'}$ represents a thienyl group or a phenyl group which may be substituted by a $C_1$-$C_5$ alkyl group or a nitro group.), and $R^8$ is a cyano group or —$CR^{22'}R^{23'}X'$ {wherein $R^{22'}$ and $R^{23'}$ each independently represent a hydrogen atom or a $C_1$-$C_5$ alkyl group, and X' represents —$NR^{24'}R^{25'}$ (wherein $R^{24'}$ and $R^{25'}$ each independently represent a $C_1$-$C_5$ alkyl group or are combined together to represent a $C_3$-$C_6$ alkylene group which may be substituted by a $C_1$-$C_5$ alkyl group.).}. Among them, more preferred are compounds in which $R^1$, $R^4$ and $R^5$ are hydrogen atoms, $R^2$ and $R^3$ each independently are —$OR^{9'}$ (wherein $R^{9'}$ represents a $C_1$-$C_5$ alkyl group.), $R^6$ is a hydrogen atom, $R^7$ is —$SO_qR^{15''}$ (wherein q' represents 2, and $R^{15''}$ represents a phenyl group which may be substituted by a $C_1$-$C_5$ alkyl group or a nitro group.), and $R^8$ is —$CR^{22''}R^{23''}X''$ (wherein $R^{22''}$ and $R^{23''}$ each independently represent a $C_1$-$C_5$ alkyl group, and X'' represents —$NR^{24''}R^{25''}$ {wherein $R^{24''}$ and $R^{25''}$ each independently represent a $C_1$-$C_5$ alkyl group.).}.

As the most preferred compound, there may be mentioned compounds in which $R^1$, $R^4$ and $R^5$ are hydrogen atoms, $R^2$ and $R^3$ are methoxy groups, $R^6$ is a hydrogen atom, $R^7$ is a phenylsulfonyl group, and $R^8$ is —$C(CH_3)_2N(C_2H_5)_2$.

As a salt which can be formed by the benzoylethylene derivative represented by the above formula (I), there may be mentioned, for example, inorganic acid salts such as carbonate, bicarbonate, hydrochloride, sulfate, phosphate, etc., or salts of organic acids such as formate, propionate, oxalate, fumarate, maleate, citrate, tartrate, benzoate, phthalate, methanesulfonate, 4-toluenesulfonate, etc., and the like.

Further, the present compound can also form a hydrate.

In the following, preferred specific examples of the compound of the present invention are shown in Table-1.

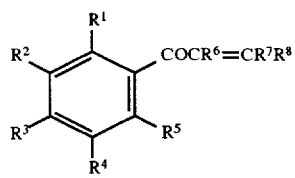

(I)

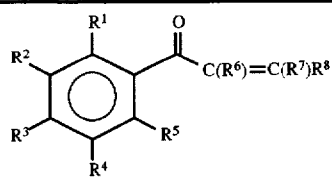

TABLE 1

| Compound No. | R¹ | R² | R³ | R⁴ | R⁵ | R⁶ | R⁷ | R⁸ |
|---|---|---|---|---|---|---|---|---|
| 1 | H | H | H | H | H | H | H | CN |
| 2 | H | H | H | H | H | H | H | CO₂Me |
| 3 | H | H | H | H | H | H | H | CO₂ⁿBu |
| 4 | H | H | H | H | H | H | H | CO₂Bn |
| 5 | H | OMe | OMe | H | H | H | H | CN |
| 6 | H | OH | OH | H | H | H | H | CN |
| 7 | H | H | OH | H | H | H | H | CN |
| 8 | H | H | OBn | H | H | H | H | CN |
| 9 | H | H | OH | H | H | H | H | CN |
| 10 | H | OMe | OH | H | H | H | H | CN |
| 11 | H | H | Cl | H | H | H | H | CN |
| 12 | H | Cl | Cl | H | H | H | H | CN |
| 13 | H | OMe | OMe | Cl | H | H | H | CN |
| 14 | H | OMe | OMe | Br | H | H | H | CN |
| 15 | H | OMe | OMe | CN | H | H | H | CN |
| 16 | H | OMe | OMe | NO₂ | H | H | H | CN |
| 17 | H | OH | OH | H | NO₂ | H | H | CN |
| 18 | H | Me | OH | Me | H | H | H | CN |
| 19 | H | Me | OMe | Me | H | H | H | CN |
| 20 | H | Me | OMe | Me | H | H | H | CO₂Me |
| 21 | H | Me | OH | Me | H | H | H | CO₂Me |
| 22 | H | H | OH | H | H | H | H | CO₂Me |
| 23 | H | OH | OH | H | H | H | H | CO₂Me |
| 24 | H | OMe | OH | H | H | H | H | CO₂Me |
| 25 | H | OMe | OBn | H | H | H | H | CO₂Me |
| 26 | H | OMe | OMe | H | H | H | H | CO₂Me |
| 27 | H | OMe | OMe | Cl | H | H | H | CO₂Me |
| 28 | H | OMe | OMe | Br | H | H | H | CO₂Me |
| 29 | H | H | OMe | H | H | H | H | CO₂Me |
| 30 | H | —OCH₂O— | | H | H | H | H | CO₂Me |
| 31 | H | H | —NMe₂ | H | H | H | H | CO₂Me |
| 32 | H | H | —NEt₂ | H | H | H | H | CO₂Me |
| 33 | H | H | SMe | H | H | H | H | CO₂Me |
| 34 | H | OMe | OMe | CN | H | H | H | CO₂Me |
| 35 | H | OMe | OMe | CF₃ | H | H | H | CO₂Me |
| 36 | H | OMe | OMe | CF₃ | NO₂ | H | H | CO₂Me |
| 37 | H | OMe | OMe | NO₂ | H | H | H | CO₂Me |
| 38 | H | OMe | OMe | NO₂ | H | H | H | CO₂Me |
| 39 | H | OMe | Cl | H | H | H | H | CO₂Me |
| 40 | H | Cl | Cl | H | H | H | H | CO₂Me |
| 41 | H | Cl | Cl | Cl | H | H | H | CO₂Me |
| 42 | H | Cl | OMe | Cl | H | H | H | CO₂Me |
| 43 | H | Cl | OH | Cl | H | H | H | CO₂Me |
| 44 | H | Me | OH | Me | H | H | H | CO₂Me |
| 45 | H | Me | OMe | Me | H | H | H | CO₂Me |
| 46 | H | Me | OMe | Me | H | H | H | CO₂ⁿBu |
| 47 | H | OMe | OMe | Me | H | H | H | CO₂ⁿBu |
| 48 | H | H | OH | Me | H | H | H | CO₂ⁿBu |
| 49 | H | H | OMe | Me | H | H | H | CO₂ⁿBu |
| 50 | H | H | Cl | Me | H | H | H | CO₂ⁿBu |
| 51 | H | OH | OH | Me | H | H | H | CO₂ⁿBu |
| 52 | H | OH | OH | Me | H | H | H | CO₂Br |
| 53 | H | OMe | OH | Me | H | H | H | CO₂Br |
| 54 | H | OMe | OBn | Me | H | H | H | CO₂Br |
| 55 | H | H | OBn | Me | H | H | H | CO₂Br |

TABLE 1-continued

| Compound No. | $R^1$ | $R^2$ | $R^3$ | $R^4$ | $R^5$ | $R^6$ | $R^7$ | $R^8$ |
|---|---|---|---|---|---|---|---|---|
| 56 | H | H | OMe | Me | H | H | H | $CO_2Br$ |
| 57 | H | H | Cl | Me | H | H | H | $CO_2Br$ |
| 58 | H | Cl | Cl | Me | H | H | H | $CO_2Br$ |
| 59 | H | Cl | H | Cl | H | H | H | $CO_2Br$ |
| 60 | H | Cl | OMe | Cl | H | H | H | $CO_2Br$ |
| 61 | H | OMe | OMe | H | H | H | H | $NH_2$ |
| 62 | H | H | OMe | H | H | H | H | $NH_2$ |
| 63 | H | H | Cl | H | H | H | H | $NH_2$ |
| 64 | H | H | OBn | H | H | H | H | $NH_2$ |
| 65 | H | OH | OH | H | H | H | H | $NH_2$ |
| 66 | H | OH | OH | H | H | H | H | NHMe |
| 67 | H | OMe | OH | H | H | H | H | NHMe |
| 68 | H | H | OH | H | H | H | H | NHMe |
| 69 | H | H | OMe | H | H | H | H | NHMe |
| 70 | H | H | Cl | H | H | H | H | NHMe |
| 71 | H | H | OBn | H | H | H | H | NHMe |
| 72 | H | H | OBn | H | H | H | H | $NEt_2$ |
| 73 | H | H | OMe | H | H | H | H | $NEt_2$ |
| 74 | H | OMe | OMe | H | H | H | H | $NEt_2$ |
| 75 | H | OMe | OBn | H | H | H | H | $NEt_2$ |
| 76 | H | OMe | OH | H | H | H | H | $NEt_2$ |
| 77 | H | H | OH | H | H | H | H | $NEt_2$ |
| 78 | H | H | Cl | H | H | H | H | $NEt_2$ |
| 79 | H | Cl | Cl | H | H | H | H | $NEt_2$ |
| 80 | H | Cl | OMe | Cl | H | H | H | $NEt_2$ |
| 81 | H | OMe | OMe | Cl | H | H | H | $NEt_2$ |

TABLE 1-continued
| Compound No. | R¹ | R² | R³ | R⁴ | R⁵ | R⁶ | R⁷ | R⁸ |
|---|---|---|---|---|---|---|---|---|
| 82 | H | OMe | OMe | CF₃ | H | H | H |  |
| 83 | H | OMe | OMe | SMe | H | H | H |  |
| 84 | H | OMe | OMe | SMe | H | H | H |  |
| 85 | H | OMe | OMe | CF₃ | H | H | H |  |
| 86 | H | OMe | OMe | H | H | H | H |  |
| 87 | H | H | OMe | H | H | H | H |  |
| 88 | H | H | OBn | H | H | H | H |  |
| 89 | H | H | Cl | H | H | H | H |  |
| 90 | H | H | H | H | H | H | H |  |
| 91 | H | OMe | OBn | H | H | H | H |  |
| 92 | H | OMe | OH | H | H | H | H |  |
| 93 | H | OMe | OH | Cl | H | H | H | 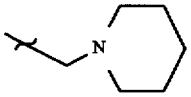 |
| 94 | H | OMe | OH | Cl | H | H | H | 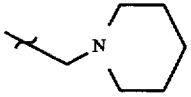 |
| 95 | H | OMe | OMe | Cl | H | H | H | 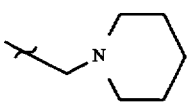 |
| 96 | H | OMe | OMe | Br | H | H | H | 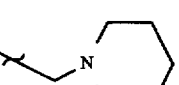 |
| 97 | H | OMe | OMe | H | H | H | H | 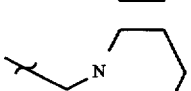 |
| 98 | H | H | OMe | H | H | H | H | 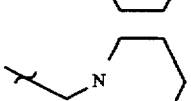 |
| 99 | H | H | Cl | H | H | H | H | |

TABLE 1-continued
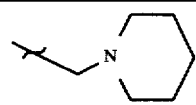
| Compound No. | R¹ | R² | R³ | R⁴ | R⁵ | R⁶ | R⁷ | R⁸ |
|---|---|---|---|---|---|---|---|---|
| 100 | H | H | NMe₂ | H | H | H | H | 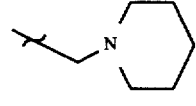 |
| 101 | H | H | OBn | H | H | H | H | 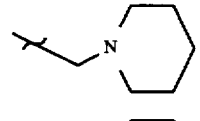 |
| 102 | H | H | CF₃ | H | H | H | H | 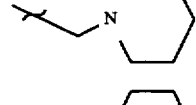 |
| 103 | H | Cl | H | Cl | H | H | H | 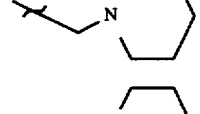 |
| 104 | H | H | —NEt₂ | H | H | H | H | 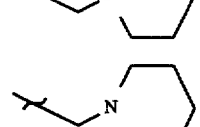 |
| 105 | H | H | SMe | H | H | H | H | 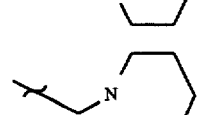 |
| 106 | H | H | —NPr₂ | H | H | H | H | 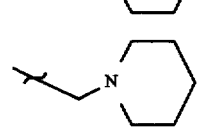 |
| 107 | H | —OCH₂O— | | H | H | H | H | 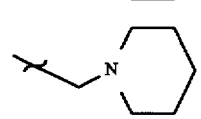 |
| 108 | H | H | OCHF₂ | H | H | H | H | 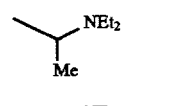 |
| 109 | H | OMe | OCHF₂ | H | H | H | H |  |
| 110 | H | OMe | OMe | H | H | H | H | 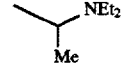 |
| 111 | H | H | OMe | H | H | H | H |  |
| 112 | H | OH | OH | H | H | H | H |  |

TABLE 1-continued
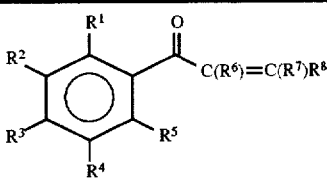
| Compound No. | R¹ | R² | R³ | R⁴ | R⁵ | R⁶ | R⁷ | R⁸ |
|---|---|---|---|---|---|---|---|---|
| 113 | H | H | Cl | H | H | H | H | 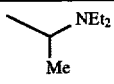 |
| 114 | H | H | H | H | H | H | H | 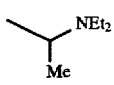 |
| 115 | H | H | H | H | H | H | H | 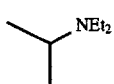 |
| 116 | H | H | OMe | H | H | H | H | 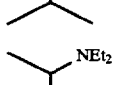 |
| 117 | H | OMe | OMe | H | H | H | H | 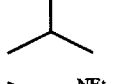 |
| 118 | H | OMe | OBn | H | H | H | H | 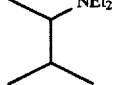 |
| 119 | H | OMe | OBn | H | H | H | H | 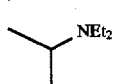 |
| 120 | H | OMe | OMe | H | H | H | H | 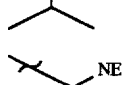 |
| 121 | H | H | OMe | H | H | H | H | 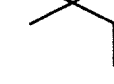 |
| 122 | H | H | Cl | H | H | H | H |  |
| 123 | H | H | H | H | H | H | H | 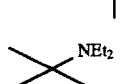 |
| 124 | H | OH | OH | H | H | H | H | 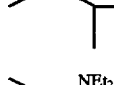 |
| 125 | H | OH | OH | H | H | H | H | 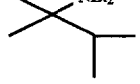 |

TABLE 1-continued
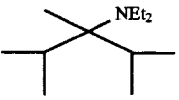
| Compound No. | R¹ | R² | R³ | R⁴ | R⁵ | R⁶ | R⁷ | R⁸ |
|---|---|---|---|---|---|---|---|---|
| 126 | H | OMe | OH | H | H | H | H | 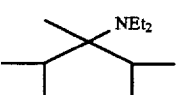 |
| 127 | H | OMe | OMe | H | H | H | H | 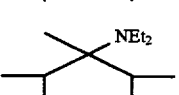 |
| 128 | H | H | OMe | H | H | H | H | 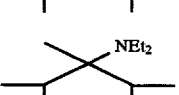 |
| 129 | H | H | Cl | H | H | H | H | 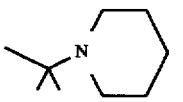 |
| 130 | H | H | Cl | H | H | H | H | 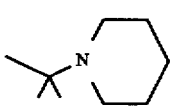 |
| 131 | H | H | OMe | H | H | H | H | 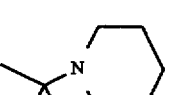 |
| 132 | H | OMe | OMe | H | H | H | H | 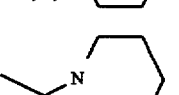 |
| 133 | H | OMe | OMe | H | H | H | H | 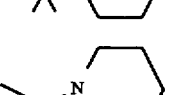 |
| 134 | H | OMe | OMe | Cl | H | H | H | 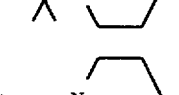 |
| 135 | H | OMe | OMe | Br | H | H | H | 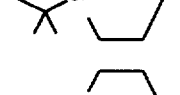 |
| 136 | H | OMe | OMe | CF₃ | H | H | H | 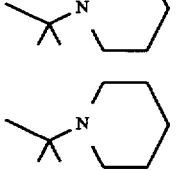 |
| 137 | H | OMe | OMe | SO₂Me | H | H | H | |

TABLE 1-continued

[Structure: phenyl ring with substituents R¹ (ortho), R² (meta), R³ (para), R⁴ (meta), R⁵ (ortho), with C(=O)-C(R⁶)=C(R⁷)R⁸ group]

| Compound No. | R¹ | R² | R³ | R⁴ | R⁵ | R⁶ | R⁷ | R⁸ |
|---|---|---|---|---|---|---|---|---|
| 138 | H | OMe | OMe | SMe | H | H | H | 1-methyl-1-(piperidin-1-yl)ethyl |
| 139 | H | OMe | OMe | NO₂ | H | H | H | 1-methyl-1-(piperidin-1-yl)ethyl |
| 140 | H | OMe | OMe | H | NO₂ | H | H | 1-methyl-1-(piperidin-1-yl)ethyl |
| 141 | H | OH | OH | H | H | H | H | 1-methyl-1-(piperidin-1-yl)ethyl |
| 142 | H | H | OH | H | H | H | H | 1-methyl-1-(piperidin-1-yl)ethyl |
| 143 | H | H | OBn | H | H | H | H | 1-methyl-1-(piperidin-1-yl)ethyl |
| 144 | H | H | H | H | H | H | H | 1-methyl-1-(piperidin-1-yl)ethyl |
| 145 | H | —OCH₂O— | | H | H | H | H | 1-methyl-1-(piperidin-1-yl)ethyl |
| 146 | H | Cl | OMe | Cl | H | H | H | 1-methyl-1-(piperidin-1-yl)ethyl |
| 147 | H | Cl | H | Cl | H | H | H | 1-methyl-1-(piperidin-1-yl)ethyl |
| 148 | H | Cl | H | Cl | H | H | H | 1-(diethylamino)cyclohexyl |
| 149 | H | H | OMe | Cl | H | H | H | 1-(diethylamino)cyclohexyl |

TABLE 1-continued

[Structure: benzene ring with R¹, R², R³, R⁴, R⁵ substituents and C(=O)–C(R⁶)=C(R⁷)R⁸ group]

| Compound No. | R¹ | R² | R³ | R⁴ | R⁵ | R⁶ | R⁷ | R⁸ |
|---|---|---|---|---|---|---|---|---|
| 150 | H | H | OMe | H | H | H | H | cyclohexyl-NEt₂ |
| 151 | H | OMe | OMe | H | H | H | H | cyclohexyl-NEt₂ |
| 152 | H | OMe | OH | H | H | H | H | cyclohexyl-NEt₂ |
| 153 | H | H | OH | H | H | H | H | cyclohexyl-NEt₂ |
| 154 | H | H | Cl | H | H | H | H | cyclohexyl-NEt₂ |
| 155 | H | H | H | H | H | H | H | cyclohexyl-NEt₂ |
| 156 | H | H | H | H | H | H | H | cyclohexyl-piperidinyl |
| 157 | H | H | OMe | H | H | H | H | cyclohexyl-piperidinyl |
| 158 | H | OMe | OMe | H | H | H | H | cyclohexyl-piperidinyl |

TABLE 1-continued

| Compound No. | R¹ | R² | R³ | R⁴ | R⁵ | R⁶ | R⁷ | R⁸ |
|---|---|---|---|---|---|---|---|---|
| 159 | H | OMe | OBn | H | H | H | H | 1-(piperidin-1-yl)cyclohexyl |
| 160 | H | H | Cl | H | H | H | H | 1-(piperidin-1-yl)cyclohexyl |
| 161 | H | H | OBn | H | H | H | H | 1-(piperidin-1-yl)cyclohexyl |
| 162 | H | —OCH₂O— | | H | H | H | H | 1-(piperidin-1-yl)cyclohexyl |
| 163 | H | —OCH₂O— | | H | H | H | H | 1-ethyl-2,2,6,6-tetramethylpiperidin-4-yl |
| 164 | H | OMe | OMe | H | H | H | H | 1-ethyl-2,2,6,6-tetramethylpiperidin-4-yl |
| 165 | H | OH | OH | H | H | H | H | 1-ethyl-2,2,6,6-tetramethylpiperidin-4-yl |
| 166 | H | H | OH | H | H | H | H | 1-ethyl-2,2,6,6-tetramethylpiperidin-4-yl |

TABLE 1-continued
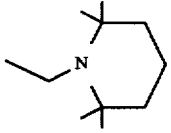
| Compound No. | R¹ | R² | R³ | R⁴ | R⁵ | R⁶ | R⁷ | R⁸ |
|---|---|---|---|---|---|---|---|---|
| 167 | H | H | Cl | H | H | H | H | 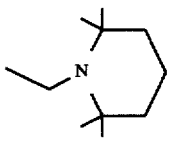 |
| 168 | H | H | H | H | H | H | H |  |
| 169 | H | H | H | H | H | H | H | 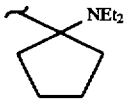 |
| 170 | H | H | OMe | H | H | H | H | 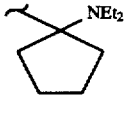 |
| 171 | H | OMe | OMe | H | H | H | H | 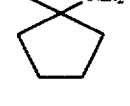 |
| 172 | H | OMe | OBn | H | H | H | H | 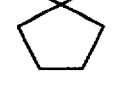 |
| 173 | H | H | OBn | H | H | H | H | 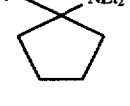 |
| 174 | H | H | Cl | H | H | H | H | 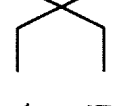 |
| 175 | H | H | Cl | H | H | H | H | 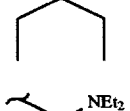 |
| 176 | H | H | OMe | H | H | H | H | 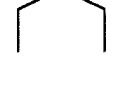 |
| 177 | H | OMe | OMe | H | H | H | H | |

TABLE 1-continued

Structure: R¹, R², R³, R⁴, R⁵ substituents on benzene ring; C(=O)–C(R⁶)=C(R⁷)R⁸

| Compound No. | R¹ | R² | R³ | R⁴ | R⁵ | R⁶ | R⁷ | R⁸ |
|---|---|---|---|---|---|---|---|---|
| 178 | H | OH | OH | H | H | H | H | -C(Me)₂-CH₂-C(Me)₂-NEt₂ |
| 179 | H | H | OH | H | H | H | H | -C(Me)₂-CH₂-C(Me)₂-NEt₂ |
| 180 | H | H | H | H | H | H | H | -C(Me)₂-CH₂-C(Me)₂-NEt₂ |
| 181 | H | H | H | H | H | CN | H | CN |
| 182 | H | H | OMe | H | H | CN | H | CN |
| 183 | H | OMe | OMe | H | H | CN | H | CN |
| 184 | H | OH | OH | H | H | CN | H | CN |
| 185 | H | H | H | H | H | CN | H | CN |
| 186 | H | H | OBn | H | H | CN | H | CN |
| 187 | H | H | Cl | H | H | CN | H | CN |
| 188 | H | H | Cl | H | H | SO₂Ph | H | CN |
| 189 | H | H | OMe | H | H | SO₂Ph | H | CN |
| 190 | H | OMe | OMe | H | H | SO₂Ph | H | CN |
| 191 | H | OMe | OH | H | H | SO₂Ph | H | CN |
| 192 | H | OMe | OBn | H | H | SO₂Ph | H | CN |
| 193 | H | OMe | OMe | H | H | SPh | H | CH |
| 194 | H | OMe | OMe | H | H | CF₃ | H | CN |
| 195 | H | OMe | OMe | H | H | CF₃ | H | CN |
| 196 | H | OMe | OMe | H | H | SOPh | H | CN |
| 197 | H | H | OMe | H | H | SOPh | H | CN |
| 198 | H | H | OMe | H | H | SOPh | H | CO₂Me |
| 199 | H | OMe | OMe | H | H | SOPh | H | CO₂Me |
| 200 | H | OH | OH | H | H | SOPh | H | CO₂Me |
| 201 | H | H | OH | H | H | SOPh | H | CO₂Me |
| 202 | H | OMe | OMe | H | H | Me | H | CO₂Me |
| 203 | H | H | H | H | H | Me | H | CO₂Me |
| 204 | H | H | OMe | H | H | SO₂Ph | H | CO₂Me |
| 205 | H | OMe | OMe | H | H | SPh | H | CO₂Me |
| 206 | H | OMe | OMe | H | H | SO₂Me | H | CO₂Me |
| 207 | H | H | Cl | H | H | SO₂Me | H | CO₂Me |
| 208 | H | H | Cl | H | H | SO₂Me | H | CO₂Bn |
| 209 | H | H | OMe | H | H | SO₂Me | H | CO₂Bn |
| 210 | H | OMe | OMe | H | H | SO₂Ph | H | CO₂Bn |
| 211 | H | OMe | OMe | H | H | Me | H | —CONHPh |
| 212 | H | H | H | H | H | Me | H | —CONHPh |
| 213 | H | H | Cl | H | H | Me | H | —CONHPh |
| 214 | H | H | Cl | H | H | CN | H | —CONH-(3-Cl-C₆H₄) |
| 215 | H | OMe | OMe | H | H | CN | H | —CONH-(3-Cl-C₆H₄) |
| 216 | H | OMe | OMe | H | H | CN | H | —CONH-(4-Cl-C₆H₄) |

TABLE 1-continued

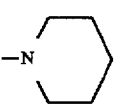

| Compound No. | R¹ | R² | R³ | R⁴ | R⁵ | R⁶ | R⁷ | R⁸ |
|---|---|---|---|---|---|---|---|---|
| 217 | H | OMe | OMe | H | H | CN | H | —CONH$_2$ |
| 218 | H | OMe | OMe | H | H | H | 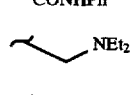 | —CONHPh |
| 219 | H | OMe | OMe | H | H | SOMe | H | —CONHPh |
| 220 | H | OMe | OMe | H | H | SO$_2$Ph | H | —CONHPh |
| 221 | H | H | OMe | H | H | SO$_2$Ph | H | —CONHPh |
| 222 | H | H | Cl | H | H | SO$_2$Ph | H | —CONHPh |
| 223 | H | —CH$_2$OCH$_2$— | | H | H | SO$_2$Ph | H | —CONHPh |
| 224 | H | OMe | OMe | H | H | H | SPh | —CONHPh |
| 225 | H | OMe | OMe | H | H | H | H | 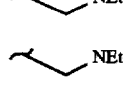 |
| 226 | H | OMe | OMe | H | H | CN | H | 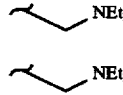 |
| 227 | H | H | OMe | H | H | CN | H | 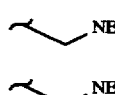 |
| 228 | H | H | Cl | H | H | CN | H | 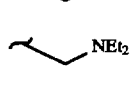 |
| 229 | H | H | OBn | H | H | CN | H | 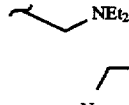 |
| 230 | H | H | OBn | H | H | SO$_2$Ph | H | 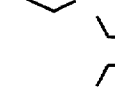 |
| 231 | H | OMe | OMe | H | H | SO$_2$Ph | H | 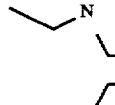 |
| 232 | H | OMe | OMe | H | H | SO$_2$Me | H | 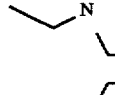 |
| 233 | H | OMe | OMe | H | H | SO$_2$CF$_3$ | H | 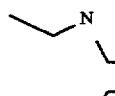 |
| 234 | H | OMe | OMe | H | H | SO$_2$CF$_3$ | H | 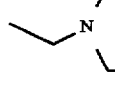 |
| 235 | H | OMe | OMe | H | H | SO$_2$Ph | H |  |
| 236 | H | H | OMe | H | H | SO$_2$Ph | H |  |
| 237 | H | H | Cl | H | H | SO$_2$Ph | H | |
| 238 | H | H | H | H | H | SO$_2$Ph | H | |

TABLE 1-continued

Structure: R1, R2, R3, R4, R5 substituted phenyl with C(=O)-C(R6)=C(R7)R8 group

| Compound No. | R¹ | R² | R³ | R⁴ | R⁵ | R⁶ | R⁷ | R⁸ |
|---|---|---|---|---|---|---|---|---|
| 239 | H | OMe | OMe | H | H | CN | H | N-piperidinyl with ethyl |
| 240 | H | H | OMe | H | H | CN | H | N-piperidinyl with ethyl |
| 241 | H | H | OBn | H | H | CN | H | N-piperidinyl with ethyl |
| 242 | H | H | OBn | H | H | SOPh | H | N-piperidinyl with ethyl |
| 243 | H | H | OMe | H | H | SOPh | H | N-piperidinyl with ethyl |
| 244 | H | OMe | OMe | H | H | SOPh | H | N-piperidinyl with ethyl |
| 245 | H | OMe | OMe | H | H | SOPh | H | C(Me)₂CH₂NEt₂ |
| 246 | H | OMe | OMe | H | H | CN | H | C(Me)₂CH₂NEt₂ |
| 247 | H | H | OMe | H | H | CN | H | C(Me)₂CH₂NEt₂ |
| 248 | H | H | Cl | H | H | CN | H | C(Me)₂CH₂NEt₂ |
| 249 | H | H | OBn | H | H | CN | H | C(Me)₂CH₂NEt₂ |
| 250 | H | H | OBn | H | H | SOPh | H | C(Me)₂CH₂NEt₂ |
| 251 | H | H | Cl | H | H | SOPh | H | C(Me)₂CH₂NEt₂ |
| 252 | H | H | OMe | H | H | SOPh | H | C(Me)₂CH₂NEt₂ |
| 253 | H | H | H | H | H | Me | Me | —CONHPh |
| 254 | H | OMe | OMe | H | H | SO₂Ph | H | C(Me)₂CH₂NEt₂ |

TABLE 1-continued

![structure](chemical structure with R1-R5 on benzene ring, C(=O)C(R6)=C(R7)R8)

| Compound No. | R¹ | R² | R³ | R⁴ | R⁵ | R⁶ | R⁷ | R⁸ |
|---|---|---|---|---|---|---|---|---|
| 255 | H | H | OMe | H | H | SO$_2$Ph | H | —C(Me)$_2$CH$_2$NEt$_2$ |
| 256 | H | —OCH$_2$O— | | H | H | SO$_2$Ph | H | —C(Me)$_2$CH$_2$NEt$_2$ |
| 257 | H | H | Cl | H | H | SO$_2$Ph | H | —C(Me)$_2$CH$_2$NEt$_2$ |
| 258 | H | H | H | H | H | SO$_2$Ph | H | —C(Me)$_2$CH$_2$NEt$_2$ |
| 259 | H | H | H | H | H | SO$_2$Me | H | —C(Me)$_2$CH$_2$NEt$_2$ |
| 260 | H | OMe | OMe | H | H | SO$_2$Me | H | —C(Me)$_2$CH$_2$NEt$_2$ |
| 261 | H | H | OMe | H | H | SO$_2$Me | H | —C(Me)$_2$CH$_2$NEt$_2$ |
| 262 | H | H | OMe | H | H | Me | H | —C(Me)$_2$CH$_2$NEt$_2$ |
| 263 | H | OMe | OMe | H | H | Me | H | —C(Me)$_2$CH$_2$NEt$_2$ |
| 264 | H | OH | OH | H | H | Me | H | —C(Me)$_2$CH$_2$NEt$_2$ |
| 265 | H | H | OH | H | H | Me | H | —C(Me)$_2$CH$_2$NEt$_2$ |
| 266 | H | H | OH | H | H | Et | H | —C(Me)$_2$CH$_2$NEt$_2$ |
| 267 | H | OMe | OMe | H | H | Et | H | —C(Me)$_2$CH$_2$NEt$_2$ |
| 268 | H | OMe | OMe | H | H | SPh | H | —C(Me)$_2$CH$_2$NEt$_2$ |
| 269 | H | OMe | OMe | H | H | H | SPh | —C(Me)$_2$CH$_2$NEt$_2$ |
| 270 | H | H | OMe | H | H | H | SPh | —C(Me)$_2$CH$_2$NEt$_2$ |
| 271 | H | H | OMe | H | H | H | SMe | —C(Me)$_2$CH$_2$NEt$_2$ |
| 272 | H | OMe | OMe | H | H | H | SMe | —C(Me)$_2$CH$_2$NEt$_2$ |
| 273 | H | OMe | OMe | H | H | H | SO$_2$Me | —C(Me)$_2$CH$_2$NEt$_2$ |

TABLE 1-continued

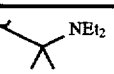

| Compound No. | R¹ | R² | R³ | R⁴ | R⁵ | R⁶ | R⁷ | R⁸ |
|---|---|---|---|---|---|---|---|---|
| 274 | H | H | OMe | H | H | H | SO$_2$Me |  |
| 275 | H | H | Cl | H | H | H | SO$_2$Me |  |
| 276 | H | H | H | H | H | H | SO$_2$Me |  |
| 277 | H | H | H | H | H | H | SO$_2$Ph | 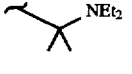 |
| 278 | H | OMe | OMe | H | H | H | SO$_2$Ph |  |
| 279 | H | H | OMe | H | H | H | SO$_2$Ph |  |
| 280 | H | H | OBn | H | H | H | SO$_2$Ph | 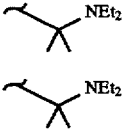 |
| 281 | H | H | Cl | H | H | H | SO$_2$Ph |  |
| 282 | H | Cl | OMe | Cl | H | H | SO$_2$Ph | 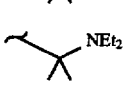 |
| 283 | H | OMe | OMe | Cl | H | H | SO$_2$Ph | 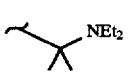 |
| 284 | H | OMe | OMe | Br | H | H | SO$_2$Ph |  |
| 285 | H | OMe | OMe | CF$_3$ | H | H | SO$_2$Ph |  |
| 286 | H | OMe | OMe | NO$_2$ | H | H | SO$_2$Ph | 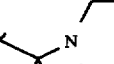 |
| 287 | H | OMe | OMe | H | H | H | H | 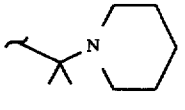 |
| 288 | H | —OCH$_2$O— | | H | H | H | SO$_2$Ph | 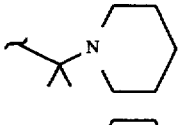 |
| 289 | H | —OCH$_2$O— | | H | NO$_2$ | H | SO$_2$Ph | 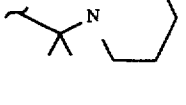 |
| 290 | H | —OCH$_2$O— | | OMe | H | H | SO$_2$Ph | |

TABLE 1-continued

[Structure: benzene ring with substituents R¹ (ortho), R² (meta), R³ (para), R⁴ (meta), R⁵ (ortho), and C(=O)C(R⁶)=C(R⁷)R⁸]

| Compound No. | R¹ | R² | R³ | R⁴ | R⁵ | R⁶ | R⁷ | R⁸ |
|---|---|---|---|---|---|---|---|---|
| 291 | H | OMe | OMe | OMe | H | H | SO$_2$Ph | piperidinyl-C(Me)$_2$- |
| 292 | H | Cl | Cl | H | H | H | SO$_2$Ph | piperidinyl-C(Me)$_2$- |
| 293 | H | OMe | OMe | H | H | H | SO$_2$-C$_6$H$_4$-Me | -C(Me)$_2$NEt$_2$ |
| 294 | H | OMe | OMe | H | H | H | SO$_2$-C$_6$H$_4$-Cl | -C(Me)$_2$NEt$_2$ |
| 295 | H | OMe | OMe | H | H | H | SOPh | -C(Me)$_2$NEt$_2$ |
| 296 | H | OMe | OMe | H | H | CF$_3$ | SOPh | -C(Me)$_2$NEt$_2$ |
| 297 | H | OMe | OMe | H | H | H | CF$_3$ | -C(Me)$_2$NEt$_2$ |
| 298 | H | OMe | OMe | H | H | H | F | -C(Me)$_2$NEt$_2$ |
| 299 | H | OMe | OMe | H | H | H | SO$_2$Ph | piperidinyl-C(Me)$_2$- |
| 300 | H | H | OMe | H | H | H | SO$_2$Ph | piperidinyl-C(Me)$_2$- |
| 301 | H | H | Cl | H | H | H | SO$_2$Ph | piperidinyl-C(Me)$_2$- |
| 302 | H | H | OBn | H | H | H | SO$_2$Ph | piperidinyl-C(Me)$_2$- |
| 303 | H | H | OBn | H | H | Me | SO$_2$Ph | piperidinyl-C(Me)$_2$- |
| 304 | H | OMe | OMe | H | H | CN | SO$_2$Ph | piperidinyl-C(Me)$_2$- |

TABLE 1-continued

| Compound No. | R¹ | R² | R³ | R⁴ | R⁵ | R⁶ | R⁷ | R⁸ |
|---|---|---|---|---|---|---|---|---|
| 305 | H | OMe | OMe | H | H | SOPh | SO$_2$Ph | CH$_2$C(Me)$_2$-piperidinyl |
| 306 | H | OMe | OMe | H | H | SO$_2$Ph | SO$_2$Ph | CH$_2$C(Me)$_2$-piperidinyl |
| 307 | H | OMe | OMe | H | H | SO$_2$Me | SO$_2$Ph | CH$_2$C(Me)$_2$-piperidinyl |
| 308 | H | OMe | OMe | H | H | SO$_2$Me | SO$_2$-C$_6$H$_4$-Me | CH$_2$C(Me)$_2$-piperidinyl |
| 309 | H | OMe | OMe | H | H | H | SO$_2$-C$_6$H$_4$-Me | CH$_2$C(Me)$_2$-piperidinyl |
| 310 | H | OMe | OMe | H | H | CN | SO$_2$-C$_6$H$_4$-Me | CH$_2$C(Me)$_2$-piperidinyl |
| 311 | H | OMe | OMe | H | H | Me | SO$_2$-C$_6$H$_4$-Me | CH$_2$C(Me)$_2$-piperidinyl |
| 312 | H | OMe | OMe | H | H | H | SO$_2$-C$_6$H$_4$-Et | CH$_2$C(Me)$_2$-piperidinyl |
| 313 | H | OMe | OMe | H | H | H | SO$_2$Me | CH$_2$C(Me)$_2$-piperidinyl |
| 314 | H | OMe | OMe | H | H | H | SO$_2$Me | CH$_2$C(Me)$_2$-piperidinyl |
| 315 | H | H | OMe | H | H | H | SO$_2$Me | CH$_2$C(Me)$_2$-piperidinyl |
| 316 | H | H | Cl | H | H | H | SO$_2$Me | CH$_2$C(Me)$_2$-piperidinyl |

TABLE 1-continued
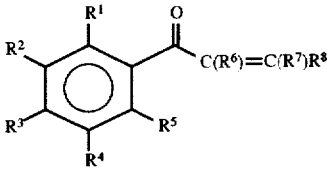
| Compound No. | R¹ | R² | R³ | R⁴ | R⁵ | R⁶ | R⁷ | R⁸ |
|---|---|---|---|---|---|---|---|---|
| 317 | H | H | Cl | H | H | H | CF$_3$ | 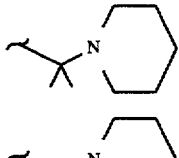 |
| 318 | H | OMe | OMe | H | H | H | CF$_3$ | 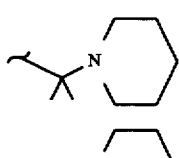 |
| 319 | H | OMe | OMe | H | H | H | F | 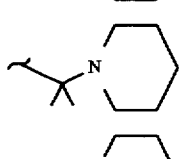 |
| 320 | H | OMe | OMe | H | H | H | SMe | 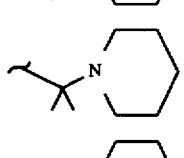 |
| 321 | H | H | OMe | H | H | H | SMe | 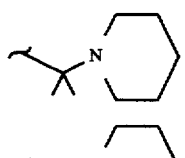 |
| 322 | H | H | Cl | H | H | H | SPh | 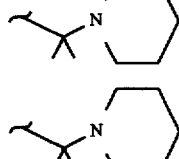 |
| 323 | H | H | Cl | H | H | H | SPh | 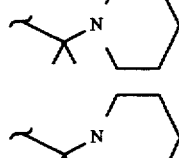 |
| 324 | H | H | OMe | H | H | H | SPh | 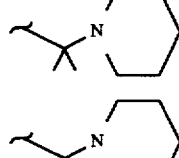 |
| 325 | H | H | OMe | H | H | SOPh | H | 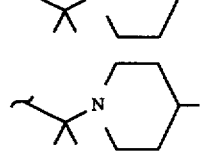 |
| 326 | H | H | OMe | H | H | SOPh | H | 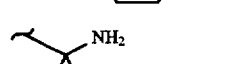 |
| 327 | H | OMe | OMe | H | H | H | SO$_2$Ph | 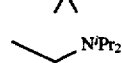 |
| 328 | H | OMe | OMe | H | H | H | SO$_2$Ph | 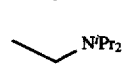 |
| 329 | H | OMe | OMe | H | H | H | SPh | N$^i$Pr$_2$ |
| 330 | H | H | OMe | H | H | H | SPh | N$^i$Pr$_2$ |

TABLE 1-continued

Structure: Benzene ring with R1, R2, R3, R4, R5 substituents and a C(=O)-C(R6)=C(R7)R8 group.

| Compound No. | R¹ | R² | R³ | R⁴ | R⁵ | R⁶ | R⁷ | R⁸ |
|---|---|---|---|---|---|---|---|---|
| 331 | H | H | Cl | H | H | H | SPh | CH₂CH₂-NiPr₂ |
| 332 | H | H | Cl | H | H | H | SOPh | CH₂CH₂-NiPr₂ |
| 333 | H | H | OMe | H | H | H | SOPh | CH₂CH₂-NiPr₂ |
| 334 | H | OMe | OMe | H | H | H | SOPh | CH₂CH₂-NiPr₂ |
| 335 | H | OMe | OMe | H | H | H | SO₂Ph | CH₂CH₂-NiPr₂ |
| 336 | H | H | OMe | H | H | H | SO₂Ph | CH₂CH₂-NiPr₂ |
| 337 | H | H | Cl | H | H | H | SO₂Ph | CH₂CH₂-NiPr₂ |
| 338 | H | H | Cl | H | H | CN | H | CH₂CH₂-NiPr₂ |
| 339 | H | OMe | OMe | H | H | CN | H | CH₂CH₂-NiPr₂ |
| 340 | H | OMe | OMe | Cl | H | CN | H | CH₂CH₂-NiPr₂ |
| 341 | H | OMe | OMe | H | H | SO₂Ph | H | CH₂CH₂-NiPr₂ |
| 342 | H | OMe | OMe | H | H | Me | H | CH₂CH₂-NiPr₂ |
| 343 | H | OMe | OMe | H | H | H | Me | CH₂CH₂-NiPr₂ |
| 344 | H | OMe | OMe | H | H | H | Me | CONHPh |
| 345 | H | H | H | H | H | H | Me | CONHPh |
| 346 | H | H | H | H | H | H | Me | CO₂Me |
| 347 | H | OMe | OMe | H | H | H | —NHMe | C(Me)₂-NEt₂ |
| 348 | H | OMe | OMe | H | H | H | —N(morpholino) | C(Me)₂-NEt₂ |
| 349 | H | OMe | OMe | H | H | H | CN | C(Me)₂-NEt₂ |
| 350 | H | OMe | OMe | H | H | H | —SO₂-C₆H₄-NO₂ | C(Me)₂-NEt₂ |
| 351 | H | OMe | OMe | H | H | H | —SO₂-C₆H₄-OMe | C(Me)₂-NEt₂ |

TABLE 1-continued

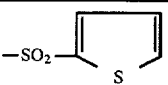

| Compound No. | $R^1$ | $R^2$ | $R^3$ | $R^4$ | $R^5$ | $R^6$ | $R^7$ | $R^8$ |
|---|---|---|---|---|---|---|---|---|
| 352 | H | OMe | OMe | H | H | H | $-SO_2-\!\!\begin{array}{c}\phantom{x}\\S\end{array}\!\!$ | $\diagup\!\!\diagdown\!\!\diagup NEt_2$ |

The compound of the present invention represented by the above formula (I) can be prepared through, for example, the following route.

(Scheme 1)

1)
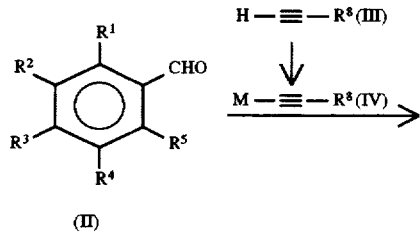

M = Li, Mgx (X = halogen atom), Na k

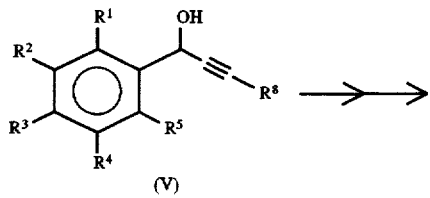

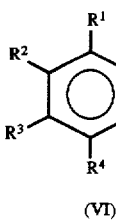

M' = Na, k, Cu, $R_2Al$ (R = alkyl)

(wherein $R^1$, $R^2$, $R^3$, $R^4$, $R^5$ and $R^8$ are as already defined.)

For example, by reacting the metal acetylide represented by the formula (IV) which can be prepared by making a base of an organometallic compound such as butyl lithium, ethyl magnesium bromide, etc., a metal alcoholate such as sodium methoxide, etc., a metal hydride such as sodium hydride, potassium hydride, etc. or the like act on the acetylene derivative represented by the above formula (III) in a suitable solvent including an ether such as tetrahydrofuran, diethyl ether, etc., a hydrocarbon such as benzene, toluene, etc., a protonic polar solvent such as methanol, ethanol, etc., an aprotic polar solvent such as dimethylsulfoxide, dimethylformamide, etc. or the like at a temperature of −100° C. to +100° C. for 5 minutes to 12 hours, with the benzaldehyde derivative represented by the formula (II) at a temperature of −100° C. to +100° C., preferably at a temperature of −80° C. to +50° C. for 5 minutes to 24 hours, preferably for 30 minutes to 12 hours, the adduct represented by the formula (V) can be prepared. By oxidizing the compound (V) in a suitable solvent, for example, in a hydrocarbon such as benzene, toluene, etc., in a polar solvent such as acetone, water, etc., in a halogenated hydrocarbon such as dichloromethane, chloroform, etc. or the like, the compound of the formula (I) can be prepared. As an oxidizer, there may be mentioned, for example, a metal oxidizer such as manganese dioxide, chromic acid, etc., and an organic oxidizer such as oxalyl chloride-trifluoroacetic acid anhydride, etc. Further, for example, by subjecting the compound (V) to a hydrogen transfer reaction using aluminum isopropoxide or zirconium chloride in a carbonyl compound such as acetone, cyclohexane, etc., the compound (VI) can be also prepared.

(Scheme 2)

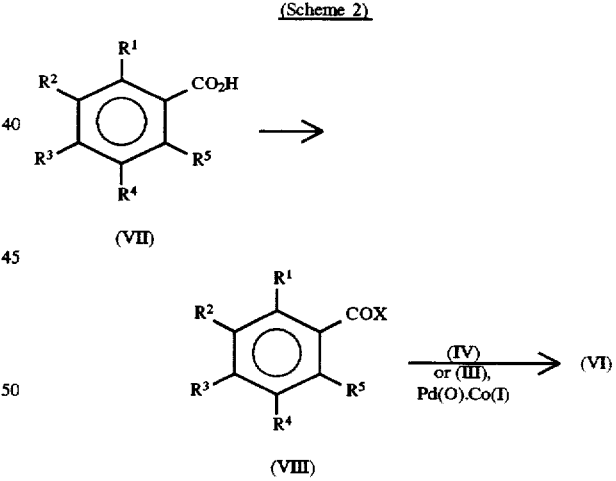

(wherein $R^1$, $R^2$, $R^3$, $R^4$ and $R^5$ are as already defined.)

Further, for example, as shown in the above Scheme 2, by reacting the acid halide compound (VIII) obtained by reacting the benzoic acid derivative represented by the formula (VII) with thionyl chloride, phosphorus pentachloride or the like in a hydrocarbon type solvent such as benzene, toluene, etc. or a halogenated hydrocarbon such as dichloromethane, chloroform, etc., with the compound (IV) in an ether such as tetrahydrofuran, diethyl ether, etc., a hydrocarbon such as benzene, toluene, etc. or a mixed solvent thereof at a temperature of −100° C. to +100° C. for 5 minutes to 24 hours, the compound (VI) can be prepared. Further, for example, by reacting the compound (VIII) with the compound (III) in the presence of catalystic amounts of a palladium complex and a copper (I) compound in a suitable solvent such as tetrahydrofuran, benzene, etc. at a temperature of +10° C. to +100° C. for 30 minutes to 48 hours, the compound (VI) can be prepared.

By reacting the compound (VI) with a 0.5 to 10 equivalent amount of a metal cyanide such as sodium cyanide, potassium cyanide, copper (I) cyanide, dialkyl aluminum cyanide, etc. in an alcohol such as ethanol, etc., a hydrocarbon such as hexane, toluene, etc., an ether such as diethyl ether, tetrahydrofuran, etc., a polar solvent such as acetone, water, etc. or a mixed solvent thereof at −70° C. to +200° C. for 0.5 to 48 hours, a compound in which $R^6$ or $R^7$ is represented by CN among the compounds of (I) can be prepared.

Further, for example, by reacting the compound (VI) with an amine represented by the following formula (IX):

$$HNR^{13}R^{14} \qquad (IX)$$

(wherein $R^{13}$ and $R^{14}$ are as defined in the formula (I)) in a polar solvent such as water, methanol, ethanol, etc., in a suitable solvent such as benzene, acetone, dimethylsulfoxide, etc. or in a mixed solvent thereof at 0° C. to 150° C. for 5 minutes to 48 hours, a compound in which $R^6$ or $R^7$ is represented by —$NR^{13}R^{14}$ (wherein $R^{13}$ and $R^{14}$ are as already defined) among the compounds of the formula (I) can be prepared.

Further, for example, when the compound (VI) is reacted with a sulfur-containing compound represented by the following formula (X) or (XI):

$$R^{15}SH \qquad (X)$$

$$R^{15}SO_2H \qquad (XI)$$

(wherein $R^{15}$ is as defined in the formula (I)) in a suitable solvent such as water, ethanol, benzene, acetone, dimethylsulfoxide, etc. at −20° C. to 150° C., a compound of the formula (I) in which $R^6$ or $R^7$ is represented by $SO_lR^{15}$ (wherein l represents 0 or 2, and $R^{15}$ is as defined in the formula (I)) can be prepared. In place of the compound represented by the formula (XI), a salt such as corresponding sodium salt, lithium salt or the like may be used depending on stability thereof, or the reaction may be carried out while generating the compound (XI) in the reaction system by adding an equivalent amount of an acid such as acetic acid, hydrochloric acid, etc. to the salt.

By reacting a compound of the formula (I) in which $R^6$ or $R^7$ is represented by $SR^{15}$ (wherein $R^{15}$ is as defined in the above formula (I)) with an inorganic oxidizer such as chromic acid, selenium dioxide, sodium metaperiodate, etc., a peracid such as m-chloroperbenzoic acid, hydrogen peroxide, peracetic acid, etc., a halogen such as iodine, bromine, etc. or the like in a halogenated hydrocarbon such as dichloromethane, chloroform, etc. or a polar solvent such as water, acetic acid, methanol, etc. at −20° C. to 100° C., a compound of the above formula (I) in which $R^6$ or $R^7$ is —$SO_mR^{15}$ (wherein m represents 1 or 2, and $R^{15}$ is as defined in the formula (I)) can be prepared.

Further, for example, by reacting the compound represented by the formula (VI) with a $C_1$-$C_5$ alkyl copper complex prepared from a 0.5 to 5 equivalent amount of copper (I) iodide or copper (I) bromide and a 0.5 to 10 equivalent amount of an organic lithium or organic magnesium compound such as $C_1$-$C_5$ alkyl lithium, $C_1$-$C_5$ alkyl magnesium bromide, etc. in a suitable solvent such as diethyl ether, tetrahydrofuran, etc. at −100° C. to +100° C. for 5 minutes to 24 hours, a compound of the formula (I) in which $R^6$ or $R^7$ is represented by a $C_1$-$C_5$ alkyl group can be prepared.

Further, for example, by, if necessary, after deprotection, oxidizing the following compound (XII) which can be prepared by reacting the compound (V) or a compound obtained by protecting the hydroxy group of the compound (V) by a suitable protective group, with (X), (XI) or the alkyl copper complex which are the above compounds in a suitable solvent such as water, ethanol, tetrahydrofuran, benzene, dimethylsulfoxide, etc. at −100° C. to +200° C. for 5 minutes to 48 hours, a compound of the formula (I) in which $R^6$ or $R^7$ is represented by a hydrogen atom can be prepared (Scheme 3)

(Scheme 3)

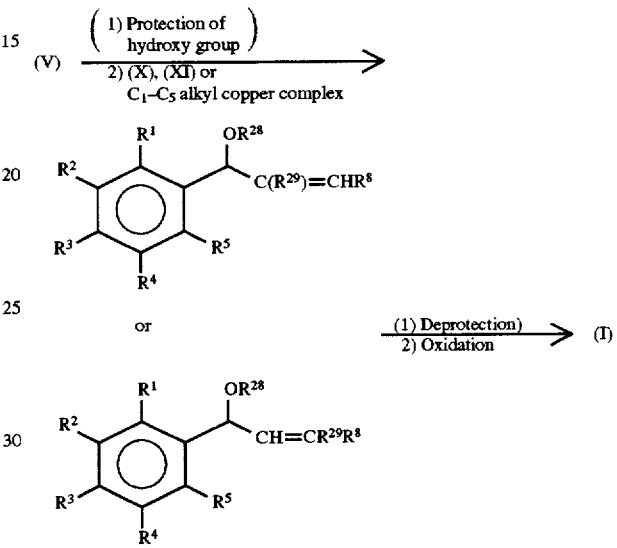

(wherein $R^1$, $R^2$, $R^3$, $R^4$, $R^5$ and $R^8$ are as already defined, $R^{28}$ represents a hydrogen atom, a 1-ethoxyethyl group, a tetrahydropyranyl group, a dimethyl-tert-butylsilyl group, etc., $R^{29}$ represents $SO_lR^{15}$ (wherein l represents 0 or 2, and $R^{15}$ represents already defined one.)

As the protective group, there may be mentioned a 1-ethoxyethyl group, a tetrahydropyranyl group, a dimethyl-tert-butylsilyl group, a benzyl group, etc., and as the oxidation conditions, the oxidation conditions from the compound (V) to (VI) used in Scheme 1 can be used.

Further, for example, when a compound of the formula (V) in which $R^8$ is represented by

[wherein $R^{22}$ and $R^{23}$ are as defined in the formula (I), and $R^{30}$ and $R^{31}$ each independently represent a hydrogen atom, a $C_1$ to $C_5$ alkyl group which may be substituted by a phenyl group or a $C_1$ to $C_5$ alkylamino group, a phenyl group which may be substituted by a halogen atom or a $C_1$ to $C_5$ alkyl group or a $C_3$ to $C_8$ cycloalkyl group, or are combined together to represent a $C_3$-$C_6$ alkylene group which may be intervened by —O— or —$NR^{27}$— (wherein $R^{27}$ is as defined in the formula (I)), or a $C_3$-$C_6$ alkylene group which may be substituted by a $C_1$-$C_5$ alkyl group.] or

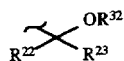

(wherein $R^{22}$ and $R^{23}$ are as defined in the formula (I), and $R^{32}$ represents a hydrogen atom or a $C_1$-$C_5$ alkyl group which may be substituted by a phenyl group.) is reduced and then oxidized as shown in the following Scheme 4. a compound in which $R^6=R^7=H$ among the compounds represented by the above formula (I) can be prepared.

(Scheme 4)

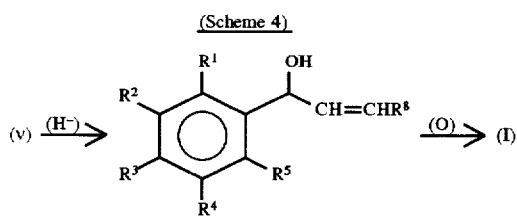

(wherein $R^1$, $R^2$, $R^3$, $R^4$, $R^5$ and $R^8$ are as already defined.)
As a reducing agent, there may be mentioned a metal hydride complex compound such as lithium aluminum hydride, etc., and as an oxidizer, there may be mentioned a metal oxidizer such as active manganese dioxide, chromic acid, etc.

para-toluenesulfonic acid, etc., a Lewis acid such as boron trifluoride, etc., and the like. As the base and the salt, there may be mentioned ammonia or a salt thereof, an organic base such as piperidine, pyridine, morpholine, 1.8-diazabicyclo-|5.4.0|-undeca-7-ene, etc. or a salt thereof, an alkali metal hydroxide such as sodium hydroxide, potassium hydroxide, etc., a metal amide such as lithium diisopropylamide, etc., a metal alcoholate such as sodium methylate, etc., an alkali metal hydride such as sodium hydride, etc., and the like.

3) Further, for example, a compound in which $R^6$ and $R^7$ are hydrogen atoms or $C_1$–$C_5$ alkyl groups, and $R^8$ is represented by —$COR^{16}$ (wherein $R^{16}$ is as defined in the formula (I)) particularly among the compounds of the formula (I) can be prepared according to the following Scheme 4.

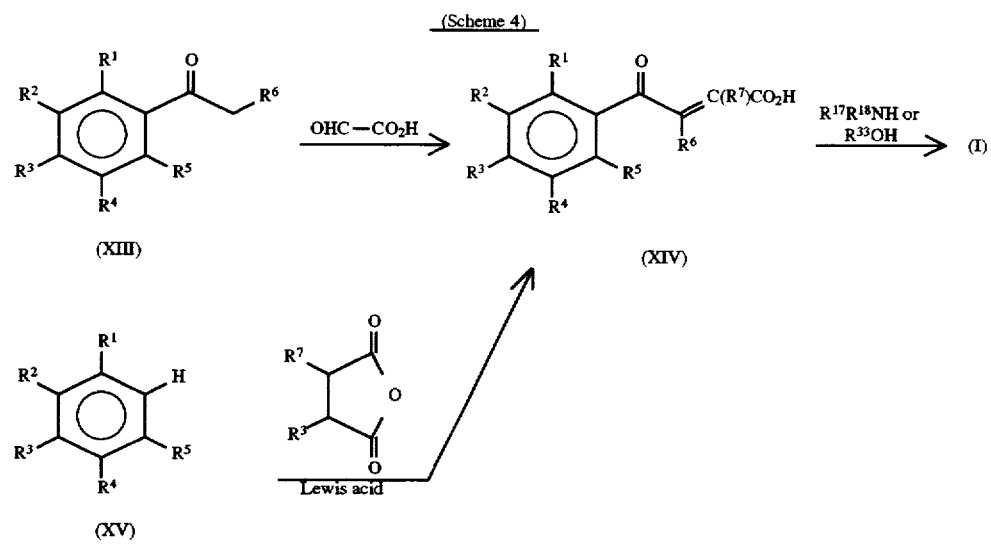

2)

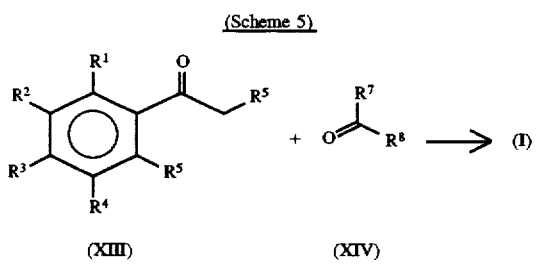

(wherein $R^1$ to $R^8$ are as defined in the formula (I).)

Further, for example, by condensing the compounds represented by the above formulae (XIII) and (XIV) in a suitable solvent such as ethanol or benzene, etc. in the presence or in the absence of a 0.01 equivalent amount to 10 equivalent amount of an acid, a base or a salt as shown in Scheme 5, it can be prepared. As the acid to be used, there may be mentioned a protonic acid such as sulfuric acid, (wherein $R^1$, $R^2$, $R^3$, $R^4$, $R^5$, $R^6$, $R^7$, $R^{17}$ and $R^{18}$ are as already defined, and $R^{33}$ represents a $C_1$–$C_5$ alkyl group which may be substituted by a phenyl group.)

For example, by reacting the acetophenone derivative represented by the above formula (XIII) with glyoxylic acid without a solvent or in a suitable solvent including a hydrocarbon type solvent such as benzene, toluene, etc., an ether type solvent such as tetrahydrofuran, dioxane, etc., and the like in the presence of a catalyst including an organic acid (the organic acid can also serve as a solvent) such as acetic acid, propionic acid, etc., an inorganic acid such as sulfuric acid, phosphoric acid, etc., and the like or without a catalyst at a temperature of −50° C. to 200° C., preferably 20° C. to 150° C. for 5 minutes to 48 hours, preferably 30 minutes to 5 hours, the benzoylacrylic acid represented by the formula (XIV) can be prepared. Further, the compound (XIV) can be also prepared by, for example, reacting the benzene or benzene derivative represented by the formula (XV) with a maleic acid anhydride derivative in the presence of a catalyst such as aluminum chloride, tin (II) chloride, etc. (under conditions of the so-called Friedel-Crafts reaction).

By condensing a compound represented by the following formula (XV) or (XVI):

$R^{17}R^{18}NH$            (XV)

R³³OH    (XVI)

(wherein $R^{17}$ and $R^{18}$ are as already defined, and $R^{33}$ represents a $C_1$-$C_5$ alkyl group which may be substituted by a phenyl group.)
to the compound (XIV) in a suitable solvent such as tetrahydrofuran, benzene, dimethylformamide, etc. or without a solvent in the presence or in the absence of a condensing agent, the compound of the present invention represented by the formula (I) can be prepared. As the condensing agent, there may be mentioned the above acids and bases, and also an inorganic condensing agent such as phosphorus oxychloride, thionyl chloride, etc., an organic condensing agent such as dicyclohexylcarbodiimide, carbonyldiimidazole, etc., and the like.

Further, for example, after the compound (XIV) is reacted with thionyl chloride, phosphorus pentachloride or the like to be converted into an acid halide, or after ethyl formate, isobutyl formate or the like is made to act on the above compound (XIV) in the presence of an organic base such as triethylamine, pyridine, etc. to be converted into an active mixed acid anhydride, by reacting said halide or anhydride with the compound (XV) or (XVI) in the presence of an organic base such as triethylamine, pyridine, etc. or an inorganic base such as sodium hydroxide, potassium hydroxide, sodium hydrogen carbonate, etc., the compound represented by the above formula (I) can be also prepared.

Further, among the compounds represented by the above formula (I), a compound in which the groups represented by $R^1$ to $R^5$ are —OH can be also prepared from the compound (I) in which corresponding $R^9$ is a $C_1$-$C_5$ alkyl group which may be substituted by a halogen atom or a phenyl group, in a suitable solvent such as methylene chloride, acetonitrile, etc. under dealkylation conditions that boron trichloride, trimethylsilane iodide, an anhydrous aluminum chloridepyridine complex or the like is made to act.

Among the compounds represented by the above formula (I), a compound in which $R^8$ is represented by CN can be also prepared by a dehydration reaction in which a compound in which $R^8$ is represented by —$CONH_2$ is reacted with thionyl chloride, dicyclohexylcarbodiimide, acetic anhydride or the like in a suitable solvent such as dimethylformamide, dimethylsulfoxide, etc. or without a solvent.

The compound represented by the above formula (I) of the present invention or a salt thereof is useful as a tyrosine kinase inhibitor as described below, and based on its effect, there can be expected uses as a carcinostatic agent, an immunosuppressant, a platelet aggregation inhibiting agent, an arteriosclerosis treating agent, an anti-inflammatory agent, etc.

As a preparation of the tyrosine kinase inhibitor or the carcinostatic agent according to the present invention, any preparation by oral, enteral or parenteral administration can be selected. As a specific preparation, there may be mentioned a tablet, a capsule, a fine granule, a syrup, a suppository, an ointment, an injection, etc.

As a carrier of the tyrosine kinase inhibitor or the carcinostatic agent according to the present invention, there may be used an organic or inorganic, solid or liquid and generally inactive pharmaceutical carrier material which is suitable for oral, enteral and other parenteral administrations. Specifically, there are, for example, crystalline cellulose, gelatin, lactose, starch, magnesium stearate, talc, vegetable and animal fat and oil, gum and polyalkylene glycol. The ratio of the tyrosine kinase inhibitor or the carcinostatic agent of the present invention to the carrier in the preparation can be changed at a ratio of 0.2% to 100%.

Further, the tyrosine kinase inhibitor or the carcinostatic agent according to the present invention may contain a tyrosine kinase inhibitor or a carcinostatic agent which is different therefrom, and other medicines. In this case, the tyrosine kinase inhibitor or the carcinostatic agent according to the present invention may not be a main ingredient in the preparation.

The tyrosine kinase inhibitor or the carcinostatic agent according to the present invention is administered generally in a dose by which a desired effect can be achieved without side effect. A specific value thereof should be determined by judgment of a doctor, but it is generally 10 mg to 10 g, preferably 20 mg to 5 g per day in the case of an adult. The compound of the present invention may be administered in a dose of 1 mg to 5 g, more preferably 3 mg to 1 g per day in the case of an adult as an active ingredient.

BEST MODE FOR PRACTICING THE INVENTION

In the following, the present invention is described in detail by referring to Examples and Test example, but the present invention is not limited by the following examples unless it exceeds its scope.

EXAMPLE 1

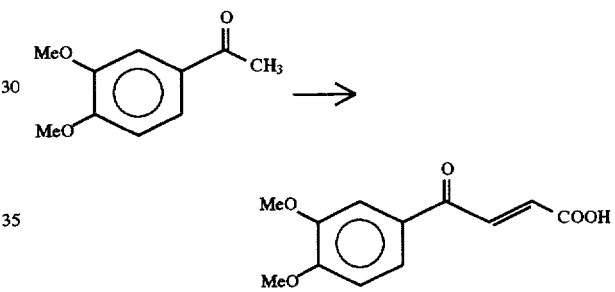

Under nitrogen atmosphere, a solution of 3,4-dimethoxyacetophenone (10.00 g, 56 mmol) and glyoxylic acid monohydrate (5.11 g, 56 mmol) dissolved in 11 ml of acetic acid was refluxed under heating for 20 hours. The reaction mixture was cooled, and the precipitated solid was collected by filtration, washed with acetic acid and then dried by heating to give 7.75 g (yield: 59%) of the above carboxylic acid.

m.p. 175° to 177° C. $^1$H NMR (DMSO, 250 MHz) δ ppm: 3.86 (s, 3H), 3.89 (s, 3H), 6.68 (d, 1H, J=15.4Hz), 7.11 (d, 1H, J=8.5Hz), 7.51 (d, 1H), 7.77 (dd, 1H, $J_1$=2.0Hz, $J_2$=7.8Hz), 7.94 (d, 1H, J=15.5Hz).

EXAMPLE 2

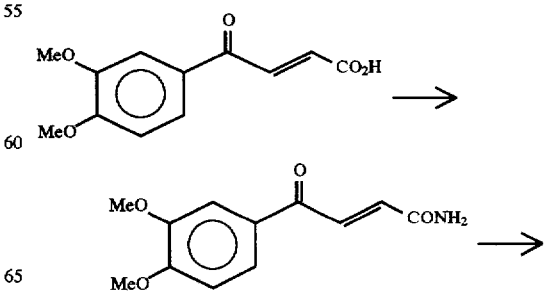

-continued

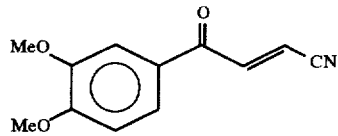

To a suspension of the above carboxylic acid (1.5 g, 6.36 mmol) obtained in Example 1 in 10 ml of carbon disulfide was added phosphorus pentachloride (1.6 g, 7.63 mmol), and the mixture was refluxed under heating for 15 minutes. A solution of the residue obtained by cooling and then concentrating the reaction mixture, dissolved in 5 ml of dichloromethane was added to 5 ml of concentrated aqueous ammonia under ice cooling. The precipitated solid was collected by filtration, washed with 1N NaOH and water in this order and then dried to give 900 mg (yield: 60%) of an amide compound.

m.p. 188° to 190° C. $^1$H NMR (250 MHz, DMSO) δ ppm: 3.85 (s, 3H), 3.88 (s, 3H), 6.95 (d, 1H, J=15.3Hz), 7.12 (d, 1H, J=9.3Hz), 7.51 (s, 1H), 7.54 (s, 1H), 7.76 (d, 1H, J=8.7Hz), 7.82 (d, 1H, J=15.5Hz), 7.85 (s, 1H).

A dimethylformamide solution (5 ml) of the amide compound (500 mg, 2.13 mmol) was stirred on an ice bath, and thionyl chloride (0.31 ml, 4.2 mmol) was added thereto. After the mixture was stirred at room temperature for 20 minutes, water was added to the reaction mixture, and the product was extracted with ethyl acetate. The residue obtained by washing the extract with brine was dried (anhydrous magnesium sulfate), concentrated and recrystallized from hexane-ethyl acetate to give a desired nitrile compound (220 mg, 47%)

m.p. 132° to 135° C., pale orange crystal $^1$H NMR (250 MHz, CDCl$_3$) δ ppm: 3.96 and 3.99 (2s, 6H), 6.57 (d, J=16.0Hz, 1H), 6.95 (d, J=8.3Hz, 1H), 7.50 to 7.70 (m, 2H), 7.84 (d, J=16.0Hz, 1H). IR (KBr) cm$^{-1}$: 3000, 3036, 2222, 1664, 1609, 1582, 1520, 1354, 1277, 1128, 772.

EXAMPLE 3

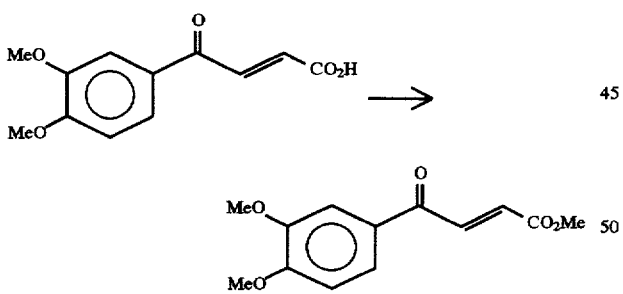

To a dichloroethane solution (6 ml) of the carboxylic acid (1.00 g, 4.24 mmol) obtained in Example 1 were added methanol (0.52 ml, 12.72 mmol) and concentrated sulfuric acid (0.014 ml), and the mixture was refluxed under heating for 2 hours. Water was added to the reaction mixture, the product was extracted with ethyl acetate, and the extract was washed with a saturated sodium hydrogen carbonate aqueous solution and then dried (anhydrous magnesium sulfate). Under reduced pressure, the solvent was removed by evaporation, and the residue was purified by silica gel column chromatography (developing solution: n-hexane/ethyl acetate=5/1) to give a desired methyl ester compound (610 mg, 57%)

m.p. 90° to 93° C., pale yellow crystal $^1$H NMR (250 MHz, CDCl$_3$) δ ppm: 3.85, 3.96 and 3.98 (3s, 9H), 6.89 (d, J=15.5Hz, 1H), 6.93 (d, J=8.4Hz, 1H), 7.58 (d, J=2.0Hz, 1H), 7.66 (dd, J=2.0, 8.4Hz, 1H), 7.95 (d, J=15.5Hz, 1H). IR (KBr) cm$^{-1}$: 2944, 2851, 1721, 1665, 1622, 1580, 1449, 1420, 1306, 1155, 1019, 766.

EXAMPLE 4

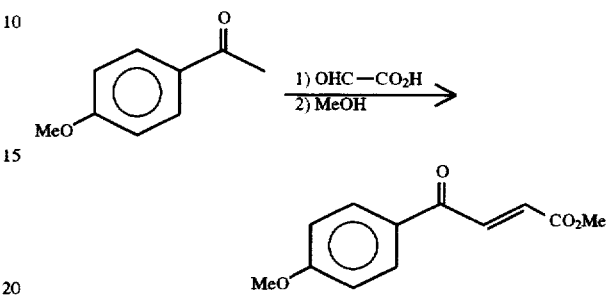

By using 4-methoxyacetophenone as a starting substance, the above methyl 2-(4-methoxybenzoyl)acrylate was obtained by the same method as in Example 1 and Example 3 (overall yield: 20%).

m.p. 75° to 76° C., pale yellow crystal IR (KBr) cm$^{-1}$: 2948, 2847, 1717, 1669, 1626, 1595, 1512, 1447, 1339, 1308, 1263, 1171, 986, 837, 768, 596.

EXAMPLE 5

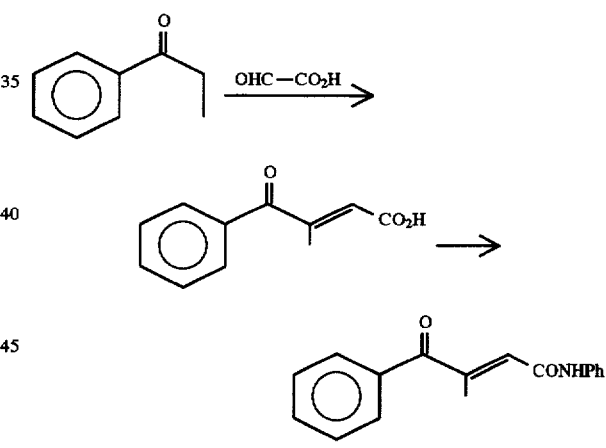

By using propiophenone as a starting substance, a reaction was carried out by the same method as in Example 1 to obtain a corresponding carboxylic acid (yield: 29%). A tetrahydrofuran solution (20 ml) of this carboxylic acid (1.04 g, 5.84 mmol) was stirred under nitrogen atmosphere, and triethylamine (0.97 ml, 7.0 mmol) and aniline (0.64 ml, 7.0 mmol) were added thereto. The reaction mixture was cooled on an ice bath, phosphorus oxychloride (0.78 ml, 8.4 mmol) was added thereto, and the mixture was stirred at room temperature overnight. Water was slowly added to the reaction mixture, the mixture was concentrated under reduced pressure, water was further added to the concentrate, and the product was extracted with ethyl acetate (70 ml). The extract was washed successively with a saturated sodium hydrogen carbonate aqueous solution, diluted hydrochloric acid and water and dried over anhydrous sodium sulfate. Under reduced pressure, the solvent was removed by evaporation, and the obtained solid was recrystallized from ethanol-water to give the desired abovementioned amide compound (170 mg, 11%).

¹H NMR (250 MHz, CDCl₃) δ ppm: 2.45 (d, J=1.3Hz, 3H), 6.26 (q, J=1.3Hz, 1H), 7.13 (t, J=7.4Hz, 1H), 7.33 (t, J=7.4Hz, 2H), 7.40 to 7.65 (m, 6H), 7.75 to 7.85 (m, 2H). m.p. 128° to 129° C., colorless needle crystal

EXAMPLE 6

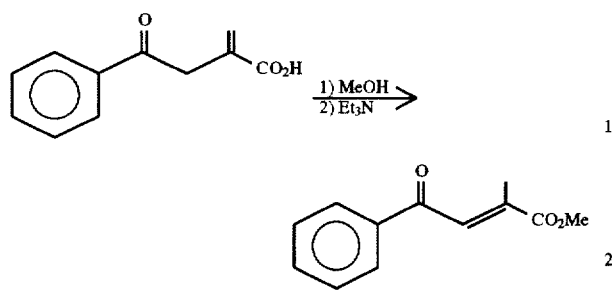

Under nitrogen atmosphere, methanol (6 ml) was cooled to −20° C., and 0.34 ml (4.7 mmol) of thionyl chloride was added thereto. After the temperature of the solution was raised to −10° C., the above carboxylic acid (560 mg, 3.14 mmol) synthesized by the method of R. E. Lutz et al. [J. Am. Chem. Soc., 75, 5039 (1953)] was added thereto. The mixture was stirred at room temperature for 3 days and then concentrated under reduced pressure to give an exo-methylene methyl ester compound (450 mg, 70%). To an ether solution (6 ml) of this exo-methylene methyl ester compound (360 mg, 1.76 mmol) was added triethylamine (2 ml), and the mixture was stirred at room temperature for 5 days. After the mixture was concentrated under reduced pressure, the residue was purified by applying it to silica gel column chromatography (developing solution: n-hexane/ethyl acetate=10/1) to give the desired above methyl ester compound (260 mg, 72%) as an oily substance.

¹H NMR (250 MHz, CDCl₃) δ ppm: 2.20 (d, J=1.3Hz, 3H), 3.86 (s, 3H), 7.45 to 7.65 (m, 3H), 7.73 (q, J=1.3Hz, 1H), 7.95 to 8.02 (m, 2H).

EXAMPLE 7

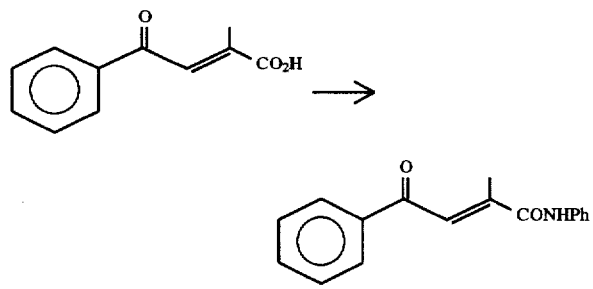

By using the above carboxylic acid synthesized by the method of R. E. Lutz et al. [J. Am. Chem. Soc., 75, 5039 (1953)], amidation was carried out by the same method as in Example 5 to give a desired anilide compound (yield: 58%).

¹H NMR (250 MHz, CDCl₃) δ ppm: 2.34 (d, J=1.4Hz, 3H), 7.17 (t, J=7.4Hz, 1H), 7.31 to 7.42 (m, 2H), 7.43 to 7.65 (m, 6H), 7.74 (brs, 1H), 7.95 to 8.03 (m, 2H). m.p. 127° to 128° C., pale yellow columnar crystal

EXAMPLE 8

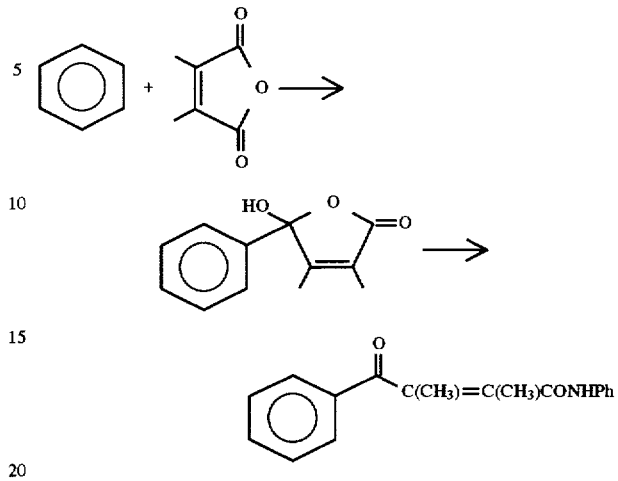

By using the above lactone compound synthesized according to the method of R. E. Lutz et al. [J. Am. Chem. Soc., 75, 5039 (1953)], amidation was carried out by the same method as in Example 5 to give a desired anilide compound (yield: 73%)

¹H NMR (250 MHz, CDCl₃) δ ppm: 1.85 and 1.89 (2d, J=0.8Hz, 6H), 6.73 (m, 2H), 6.85 (t, J=7.4Hz, 1H), 7.11 (t, J=7.9Hz, 2H), 7.37 (m, 3H), 7.52 (m, 2H). m.p. 218° to 221° C., white crystal

EXAMPLE 9

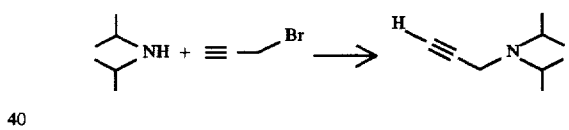

Under nitrogen atmosphere, an acetone suspension (15 ml) of diisopropylamine (4.05 g, 40.0 mmol) and potassium carbonate (6.91 g, 50.0 mmol) was cooled to 5° C., and while stirring the suspension, propargyl bromide (3.01 ml, 40.0 mmol) was added thereto. After the temperature of the reaction mixture was raised to room temperature over 2 hours, the mixture was further stirred at room temperature for 3 hours. To the residue obtained by removing precipitates by filtration and concentrating the filtrate was added water, and the product was extracted with dichloromethane (50 ml). After the extract was dried over sodium sulfate, the solvent was removed by evaporation under reduced pressure to give oily propargylamine (2.78 g, yield: 50%).

¹H NMR (250 MHz, CDCl₃) δ ppm: 1.10 (d, J=6.5Hz, 12H), 2.13 (t, J=2.5Hz, 1H), 3.20 (hep, J=6.5Hz, 2H), 3.42 (d, J=2.5Hz, 2H).

EXAMPLE 10

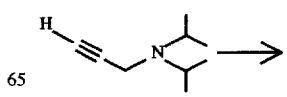

-continued

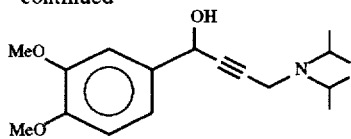

Under nitrogen atmosphere, a tetrahydrofuran solution (40 ml) of the propargylamine (1.39 g, 10.0 mmol) obtained in Example 9 was cooled to -70° C., and while stirring the solution, a 1.56M n-butyl lithium solution was added dropwise thereto. After the temperature of the reaction solution was slowly raised to 0° C., the solution was cooled to -70° C., and a tetrahydrofuran solution (10 ml) of 3,4-dimethoxybenzaldehyde (1.66 g, 10.0 mmol) was added dropwise thereto. After the temperature of the reaction mixture was raised to 0° C. over 2 hours, water was added thereto to terminate the reaction. Under reduced pressure, the solvent was removed by evaporation, and then the product was extracted with dichloromethane (40 ml×2). After the extract was dried over anhydrous sodium sulfate, the solvent was removed by evaporation under reduced pressure. The residue was purified by silica gel column chromatography (CHCl₃:MeOH=20:1) to give the above-mentioned amino-alcohol (3.00 g, yield: 98%) as an oily substance.

$^1$H NMR (250 MHz, CDCl₃) δ ppm: 1.10 (d, J=6.5Hz, 12H), 2.40 (brs, 1H), 3.20 (hep, J=6.5Hz, 2H), 3.51 (d, J=1.7Hz, 2H), 3.89 and 3.90 (2s, 6H), 5.42 (brs, 1H), 6.85 (d, J=8.1Hz, 1H), 7.07 (m, 2H)

EXAMPLE 11

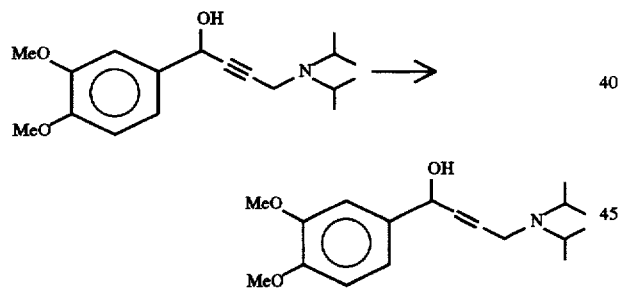

A tetrahydrofuran solution (10 ml) of the propargyl alcohol (1.02 g, 3.10 mmol) obtained in Example 10 was added dropwise to an ether solution (30 ml) of 330 mg (8.7 mmol) of lithium aluminum hydride cooled to -30° C. After the mixture was stirred at room temperature for 2 days, water (1 ml) was slowly added to the reaction mixture while ice cooling. After the mixed solution was stirred at room temperature for a while, insolubles was filtered with celite, and the filtrate was concentrated. The residue was purified by silica gel column chromatography (developing solution: chloroform/methanol=30/1 to 5/1) to give an allyl alcohol compound (719 mg, 76%)

$^1$H NMR (250 MHz, CDCl₃) δ ppm: 1.05 (d, J=6.6Hz, 12H), 2.10 (brs, 1H), 3.11 (hep, J=6.6Hz, 2H), 3.18 (d, J=3.8Hz, 2H), 3.87 and 3.88 (2s, 6H), 5.17 (m, 1H), 5.83 (m, 1H), 6.80 to 6.95 (m, 3H).

EXAMPLE 12

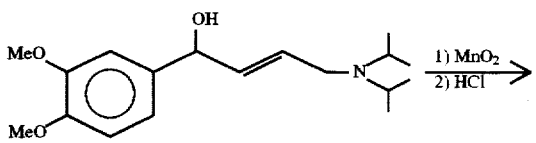

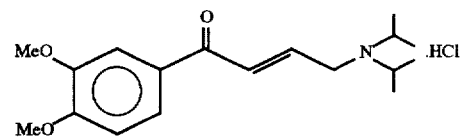

A dichloromethane solution (50 ml) of the allyl alcohol compound (710 mg, 2.32 mmol) synthesized in Example 11 was vigorously stirred at room temperature, and active manganese dioxide (7.1 g) was gradually added thereto. After stirring was continued for 1.5 hours, the reaction mixture was filtered with celite, and the filtrate was concentrated to give a ketone compound (450 mg, 64%).

$^1$H NMR (250 MHz, CDCl₃) δ ppm: 1.03 (d, J=6.5Hz, 12H), 3.06 (hep, J=6.5Hz, 2H), 3.34 (d, J=4.4Hz, 2H), 3.95 (s, 6H), 6.91 (d, J=8.2Hz, 1H), 7.06 (dt, J=15.1, 4.4Hz, 1H), 7.19 (d, J=15.1Hz, 1H), 7.55 to 7.65 (m, 2H).

An ether solution (8 ml) of the obtained ketone compound (116 mg, 0.38 mmol) was cooled with ice, a 7% by weight of hydrogen chloride acetic acid solution (0.7 ml) was added thereto, and the mixture was stirred at the same temperature for 15 minutes. Precipitated amine hydrochloride (109 mg, 84%) was isolated by filtration.

$^1$H NMR (250 MHz, DMSO-d) δ ppm: 1.33 and 1.36 (2d, J=11.0Hz, 12H), 3.69 (m, 2H), 3.85 and 3.87 (2s, 6H), 4.10 (m, 2H), 7.05 (dd, J=6.8, 15.1Hz, 1H), 7.13 (d, J=8.5Hz, 1H), 7.53 (d, J=1.7Hz, 1H), 7.65 to 7.80 (m, 2H).

EXAMPLE 13

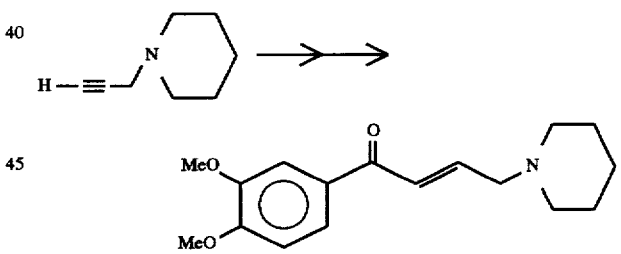

By using 3-piperidinepropyne (Japanese Provisional Patent Publication No. 98755/1979) as a starting substance, the above amine compound was obtained by the same method as in Examples 10 to 12 (overall yield: 20%).

$^1$H NMR (250 MHz, CDCl₃) δ ppm: 1.40 to 1.55 (m, 2H), 1.62 (m, 4H), 2.45 (m, 4H), 3.22 (m, 2H), 3.95 and 3.96 (2s, 6H), 6.90 (d, J=8.3Hz, 1H), 7.00 to 7.10 (m, 2H), 7.50 to 7.70 (m, 2H).

To an acetone solution (5 ml) of the obtained amine compound (360 mg, 1.30 mmol) was added an acetone solution (10 ml) of fumaric acid (75 mg, 0.65 mmol), and the mixture was stirred at room temperature for 30 minutes. The precipitated crystal was collected by filtration and washed with acetone to give fumarate of the above amine compound (180 mg, 35%).

$^1$H NMR (250 MHz, DMSO-d) δ ppm: 1.35 to 1.50 (m, 2H), 1.50 to 1.63 (m, 4H), 2.45 to 2.65 (m, 4H), 3.34 (d, J=6.3Hz, 2H), 3.81 and 3.84 (2s, 6H), 6.57 (s, 2H), 6.83 (dt, J=15.3, 6.3Hz, 1H), 7.07 (d, J=8.5Hz, 1H), 7.30 (d, J=15.3Hz, 1H), 7.47 (d, J=1.8Hz, 1H), 7.67 (dd, J=1.8, 8.5Hz, 1H). m.p. 143° to 144° C., colorless powder crystal IR (KBr) cm$^{-1}$: 3449, 2946, 2773, 2596, 1671, 1626, 1581, 1518, 1424, 1393, 1354, 1277, 1242, 1204, 1157, 1022, 766, 632.

EXAMPLE 14

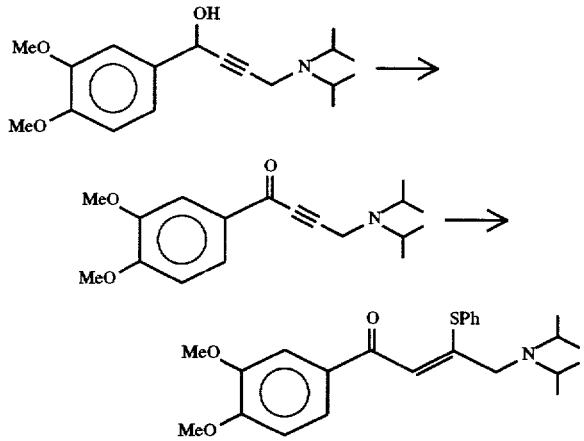

A dichloromethane solution (50 ml) of the amino-alcohol (1.20 g, 3.93 mmol) obtained in Example 10 was vigorously stirred at room temperature, and active manganese dioxide (12.0 g) was added to this solution. After 1 hour, insolubles were removed by filtration, and the filtrate was concentrated under reduced pressure to give the above ynone compound (715 mg, yield: 60%) which was a desired compound, as a brown oily substance.

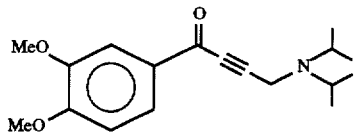

$^1$H NMR (250 MHz, CDCl$_3$) δ ppm: 1.16 (d, J=6.5Hz, 6H), 3.27 (sep, J=6.5Hz, 1H), 3.73 (s, 2H), 3.94 and 3.97 (2s, 6H), 6.94 (d, J=8.5Hz, 1H), 7.62 (d, J=1.8Hz, 1H), 7.84 (dd, J=1.8, 8.5Hz, 1H).

To an ether solution (5 ml) of the obtained ynone compound (320 mg, 1.05 mmol) were added thiophenol (110 µl, 1.07 mmol) and a trace amount of piperidine, and the mixture was stirred at room temperature for 4 hours. Under reduced pressure, the mixture was concentrated, and the residue was purified by silica gel column chromatography (developing solution: n-hexane/ethyl acetate=2/1) to give a thiophenol adduct (219 mg, 50%) which was a desired substance.

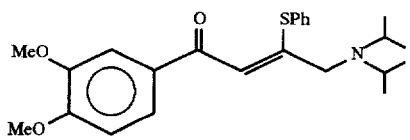

$^1$H NMR (250 MHz, CDCl$_3$) δ ppm: 0.91 (d, J=6.6Hz, 12H), 2.97 (hep, J=6.6Hz, 2H), 3.02 (d, J=1.4Hz, 2H), 3.96 (s, 6H), 6.93 (d, J=8.3Hz, 1H), 7.35 to 7.45 (m, 3H), 7.55 to 7.70 (m, 4H), 7.81 (t, J=1.4Hz, 1H). m.p. 120° to 122° C., pale yellow crystal

EXAMPLE 15

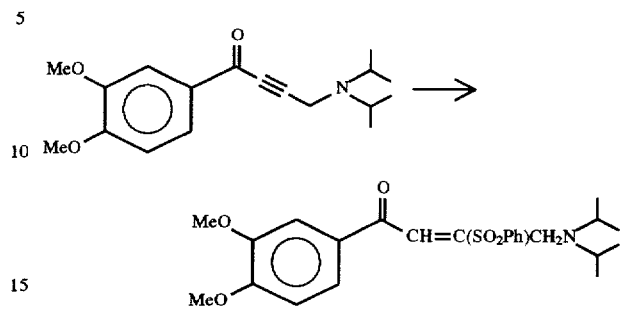

To an ethanol solution (4 ml) of the ynone compound (120 mg, 0.38 mmol) obtained in Example 14 and sodium benzenesulfinate (76 mg, 0.38 mmol) was added acetic acid (25 µl, 0.42 mmol) at room temperature, and the mixture was stirred at room temperature for 3 hours. To the reaction mixture were added water (10 ml) and saturated sodium hydrogen carbonate aqueous solution (10 ml), and the product was extracted with chloroform (20 ml). The extract was dried (anhydrous sodium sulfate) and concentrated, and the residue was purified by silica gel chromatography to give the desired above-mentioned vinyl sulfone compound (93 mg, 55%)

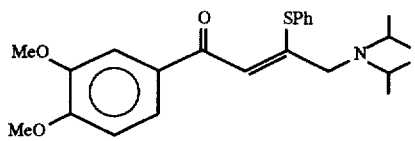

$^1$H NMR (250 MHz, CDCl$_3$) δ ppm: 0.90 (d, J=6.5Hz, 12H), 2.95 (hep, J=6.5Hz, 2H), 3.32 (s, 2H), 3.95 and 3.97 (2s, 6H), 6.94 (d, J=8.4Hz, 1H), 7.42 (brs, 1H), 7.45 to 7.70 (m, 5H), 7.96 to 8.05 (m, 2H). m.p. 167° to 169° C., orange powder crystal IR (KBr) cm$^{-1}$: 2972, 1651, 1586, 1514, 1466, 1421, 1318, 1271, 1213, 1173, 1146, 1088, 1017, 762, 729, 615, 602, 557.

EXAMPLE 16

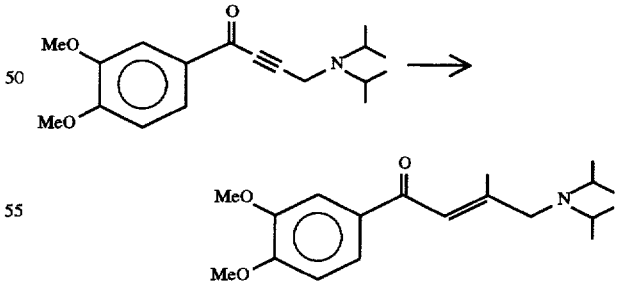

Under nitrogen atmosphere, to a tetrahydrofuran solution (15 ml) of cuprous cyanide (179 mg, 2.0 mmol) was added dropwise a 1.5M methyl lithium ether solution (2.7 ml, 4.0 mmol) at −50° C., and the mixture was stirred for 2 minutes. The solution was cooled to −70° C., and a tetrahydrofuran solution (6 ml) of the ynone compound (289 mg, 0.95 mmol) obtained in Example 14 was added dropwise thereto. After the temperature of the reaction mixture was slowly raised to room temperature, the mixture was cooled to 0° C., and a saturated ammonium chloride aqueous solution and aqueous ammonia were added thereto. After the product was extracted with ether (20 ml×2) and dried (anhydrous sodium sulfate), the solvent was removed by evaporation under reduced pressure. The residue was purified by silica gel column chromatography (developing solution: n-hexane/ethyl acetate=2/1) to give the above-mentioned desired compound (160 mg, 53%) as an oily substance.

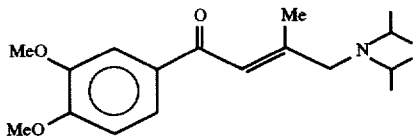

¹H NMR (250 MHz, CDCl₃) δ ppm: 1.03 (d, J=6.6Hz, 12H), 2.11 (s, 3H), 3.04 (hep, J=6.6Hz, 2H), 3.15 (s, 2H), 3.95 (s, 6H), 6.91 (d, J=8.1Hz, 1H), 7.23 (m, 1H), 7.57 (s, 1H), 7.59 (dd, J=1.9, 8.1Hz, 1H).

EXAMPLE 17

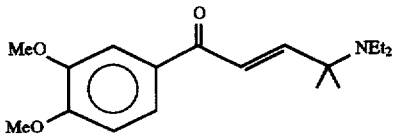

By using the above-mentioned 3-(diethylamino)-3-methylbutyne prepared according to the method of A. P. Poisselle et al. [J. Org. Chem., 26, 725 (1961)] and the method of R. S. Hznzel et al. [J. Am. Chem. Soc., 82, 4908 (1960)] as a starting substance, the above-mentioned amine compound was obtained by the same method as in Examples 10 to 12 (overall yield: 59%)

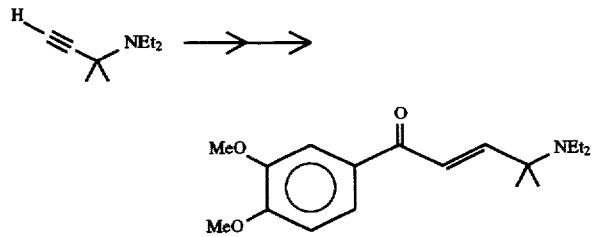

¹H NMR (250 MHz, CDCl₃) δ ppm: 1.06 (t, J=7.1Hz, 6H), 1.28 (s, 6H), 2.58 (q, J=7.1Hz, 4H), 3.95 and 3.96 (2s, 6H), 6.87 (d, J=15.7Hz, 1H), 6.91 (d, J=8.0Hz, 1H), 7.09 (d, J=15.7Hz, 1H), 7.55 to 7.62 (m, 2H).

An ether solution of the above-mentioned amine compound obtained (100 mg, 0.33 mmol) was cooled with ice, a 7% hydrochloric acid ethyl acetate solution (2 ml) was added thereto, and the mixture was stirred at the same temperature for 15 minutes. The precipitated solid was collected by filtration and dried to give hydrochloride of the above-mentioned amine compound (75 mg, 67%).

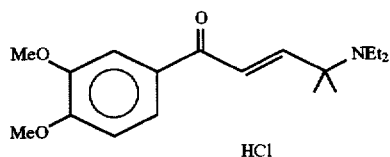

¹H NMR (250 MHz, CDCl₃) δ ppm: 1.57 (t, J=7.4Hz, 6H), 1.83 (s, 6H), 3.05 and 3.46 (2m, 4H), 3.97 and 3.99 (2s, 6H), 6.96 (d, J=8.5Hz, 1H), 7.11 (d, J=15.7Hz, 1H), 7.63 (d, J=15.7Hz, 1H), 7.63 (d, J=1.9Hz, 1H), 7.77 (dd, J=1.9, 8.5Hz, 1H), 11.82 (brs, 1H). m.p. 214° to 215° C., white powder crystal

EXAMPLE 18

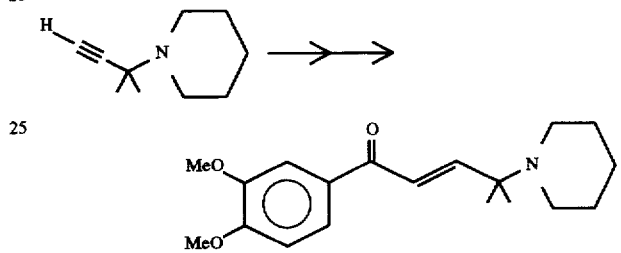

By using 3-piperidine-3-methyl-butyne as a starting substance, the above-mentioned amine compound (overall yield: 24%) and hydrochloride (yield: 73%) were obtained by the same method as in Example 17. The respective data are shown below.

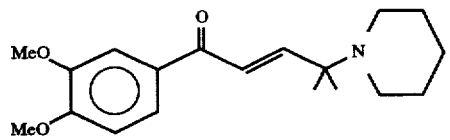

¹H NMR (250 MHz, CDCl₃) δ ppm: 1.25 (s, 6H), 1.40 to 1.50 (m, 2H), 1.50 to 1.65 (m, 4H), 2.53 (m, 4H), 3.95 and 3.96 (2s, 6H), 6.88 (d, J=15.4Hz, 1H), 6.91 (d, J=8.0Hz, 1H), 7.07 (d, J=15.7Hz, 1H), 7.50 to 7.62 (m, 2H). Pale yellow oily substance

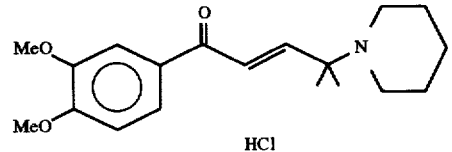

¹H NMR (250 MHz, CDCl₃) δ ppm: 1.79 (s, 6H), 1.80 to 2.00 (m, 4H), 2.45 to 2.80 (m, 4H), 3.60 to 3.75 (m, 2H), 3.97 and 3.99 (2s, 6H), 6.96 (d, J=8.4Hz, 1H), 7.07 (d, J=15.7Hz, 1H), 7.54 (d, J=15.7Hz, 1H), 7.62 (d, J=1.9Hz, 1H), 7.75 (dd, J=1.9, 8.4Hz, 1H), 12.10 (brs, 1H). m.p. 255° C. (dec), colorless powder crystal

EXAMPLE 19

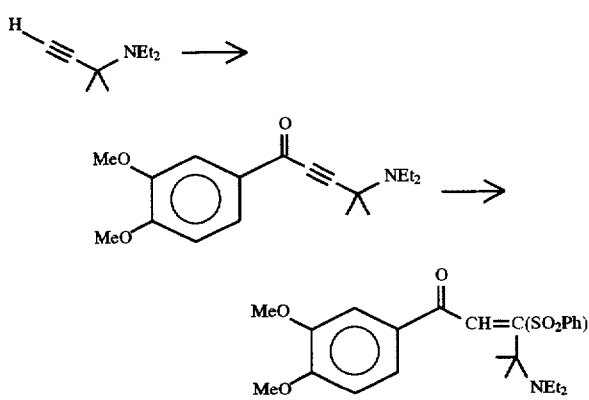

By using 3-dimethylamino-3-methylbutyne as a starting substance, the above-mentioned ynone compound was synthesized (see Example 10 and Example 14, overall yield: 64%), and further a vinyl sulfone compound (yield: 46%) was obtained by the same method as in Example 15.

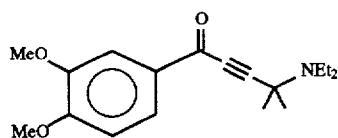

$^1$H NMR (250 MHz, CDCl$_3$) δ ppm: 1.13 (t, J=7.1Hz, 6H), 1.54 (s, 6H), 2.78 (q, J=7.1Hz, 4H), 3.95 and 3.97 (2s, 6H), 6.94 (d, J=8.4Hz, 1H), 7.63 (d, J=1.9Hz, 1H), 7.84 (dd, J=1.9, 8.4Hz, 1H).

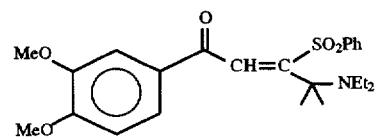

$^1$H NMR (250 MHz, CDCl$_3$) δ ppm: 0.96 (t, J=7.1Hz, 6H), 1.35 (s, 6H), 2.41 (q, J=7.1Hz, 4H), 3.96 (s, 6H), 6.96 (d, J=8.2Hz, 1H), 7.45 to 7.70 (m, 5H), 7.84 (s, 1H), 8.05 to 8.10 (m, 2H). m.p. 133° to 134° C., pale yellow powder crystal IR (KBr) cm$^{-1}$: 2975, 2938, 1655, 1597, 1586, 1512, 1449, 1418, 1306, 1269, 1209, 1169, 1146, 1086, 1020, 756, 741, 694, 642, 561.

REFERENCE EXAMPLE 1

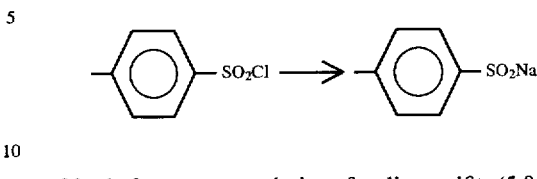

20 ml of an aqueous solution of sodium sulfite (5.0 g, 39.9 mmol) and sodium hydrogen carbonate (3.5 g, 42.0 mmol) was heated to 80° C. by an oil bath, p-toluenesulfonyl chloride (4.0 g, 21.0 mmol) was added thereto, and the mixture was heated at 80° C. for 4 hours. After cooling, crystal was collected by filtration and dried under reduced pressure. The crystal was used for the next reaction without carrying out further purification. (yielded amount: 2.7 g, yield: 72%)

$^1$H NMR (250 MHz, DMSO-d$_6$) δ ppm: 2.29 (s, 3H), 7.12 (d, J=7.9Hz, 2H), 7.38 (d, J=7.9Hz, 2H). Colorless powder In the same manner as in Reference example 1, the compounds of Reference examples 2 to 4 were prepared by using commercially available sulfonic acid chlorides. In the following, the structures of the used acid chlorides and the desired compounds and the physical properties and yields of the desired compounds are shown.

| Reference example No. | Sulfonic acid chloride | Sodium sulfinate | $^1$H-NMR (250 MHz, DMSO-d$_6$) δ (ppm) | Yield (%) |
|---|---|---|---|---|
| 2 | NO$_2$-C$_6$H$_4$-SO$_2$Cl | NO$_2$-C$_6$H$_4$-SO$_2$Na | 7.71(d, J=8.7Hz, 2H), 8.12(d, J=8.6Hz, 2H) | 69 |
| 3 | thiophene-SO$_2$Cl | thiophene-SO$_2$Na | 6.92 to 6.97 (m, 2H), 7.40 (d, J=4.5Hz, 1H) | 75 |
| 4 | MeSO$_2$Cl | MeSO$_2$Na | 1.95(s, 3H) | 20 |

EXAMPLE 20

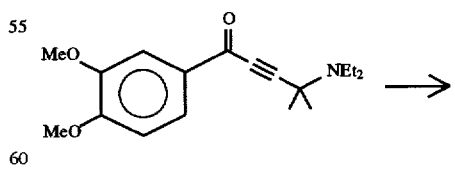

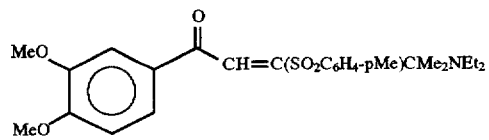

Acetic acid (75 ml, 1.32 mmol) was added to an ethanol solution (10 ml) of the ynone compound (400 mg, 1.32 mmol) obtained in Example 19 and sodium p-toluenesulfinate (350 mg, 1.98 mmol) obtained in Reference example 1 at room temperature, and the mixture was stirred at room temperature for 24 hours. After completion of the reaction, the solvent was concentrated under reduced pressure, then 20 ml of water was added to the concentrate, and the mixture was extracted twice with each 20 ml of chloroform. The organic layer was washed with a saturated sodium hydrogen carbonate aqueous solution and a saturated saline solution, dried over anhydrous sodium sulfate and then filtered. The residue obtained after concentration under reduced pressure was applied to silica gel column chromatography (n-hexane-ethyl acetate=3:1) to give a vinyl sulfone compound (280 mg, 46%) from a desired fraction.

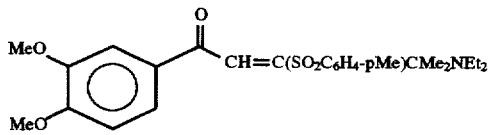

$^1$H NMR (250 MHz, CDCl$_3$) δ ppm: 0.98 (t, J=7.1Hz, 6H), 1.34 (s, 6H), 2.42 (t, J=7.0Hz, 4H), 2.43 (s, 3H), 3.96 (s, 6H), 6.95 (d, J=8.3Hz, 1H), 7.33 (d, J=8.1Hz, 2H), 7.50 (dd, J=8.3, 1.9Hz, 1H), 7.58 (d, J=1.8Hz, 1H), 7.82 (s, 1H), 7.94 (d, J=8.3Hz, 2H). m.p. 75° to 77° C., colorless powder IR (KBr) cm$^{-1}$: 2971, 1659, 1595, 1514, 1464, 1418, 1306, 1269, 1144, 1024, 818, 758, 723.

By using the sodium sulfinates prepared in Reference examples 2 to 4 and the ynone compound obtained in Example 19, the compounds of Examples 21 to 23 were prepared in the same manner as in the method of Example 20. In the following, the structures of the sodium sulfinates used and the desired compounds and the physical properties and yields of the desired compounds are shown.

| Example No. | Sodium sulfinate | Desired compound | $^1$H-NMR 250MHz, CDCl$_3$ δppm | IR(kBr)cm$^{-1}$ | Yield (%) |
|---|---|---|---|---|---|
| 21 | NO$_2$—C$_6$H$_4$—SO$_2$Na | MeO, MeO-C$_6$H$_2$-C(O)CH=C(CMe$_2$NEt$_2$)SO$_2$—C$_6$H$_4$—NO$_2$ | 0.90(t, J=7.1Hz, 6H), 1.42 (s, 6H), 2.39(q, J=7.1Hz, 4H), 3.95(s, 3H), 3.97(s, 3H), 6.96(d, 1H), 7.47(dd, J=8.3, 1.9Hz, 1H), 7.56(d, J=1.9Hz, 1H), 7.82(s, 1H), 8.32(d, J=9.0Hz, 2H), 8.39(d, J=9.0Hz, 2H) | 3430, 2969, 2363, 1657, 1597, 1532, 1514, 1470, 1499, 1352, 1304, 1271, 1020, 748 m.p. 120–122° C. | Yellow powder 10 |
| 22 | thiophene-SO$_2$Na | MeO, MeO-C$_6$H$_2$-C(O)CH=C(CMe$_2$NEt$_2$)SO$_2$-thiophene | 1.01(t, J=7.1Hz, 6H), 1.45 (s, 6H), 2.50(q, J=7.1Hz, 4H), 3.95(s, 6H), 6.94(d, J=8.3Hz, 1H), 7.13(dd, J=5.0, 3.8Hz, 1H), 7.47(d, J=8.3Hz, 1H), 7.56(d, J=2.0Hz, 1H), 7.68(dd, J=5.0, 1.4Hz, 1H), 7.81(s, 1H), 7.89(dd, J=4.0, 1.4Hz, 1H) | 3449, 3100, 2975, 2824, 1736, 1653, 1599, 1586, 1512, 1466, 1418, 1314, 1269, 1211, 1167, 1140 m.p. 151–152° C. | Colorless powder |
| 23 | MeSO$_2$Na | MeO, MeO-C$_6$H$_2$-C(O)CH=C(CMe$_2$NEt$_2$)SO$_2$Me | 1.09(t, J=7.1Hz, 6H), 1.59 (s, 6H), 2.70(q, J=7.1Hz, 4H), 3.14(s, 3H), 3.94(s, 6H), 6.91(d, J=8.3, Hz, 1H), 7.40(dd, J=8.3, 1.9Hz, 1H), 7.44(s, 1H), 7.50(d, J=1.9Hz, 1H) | 3432, 2971, 2936, 2866, 1661, 1597, 1512, 1458, 1413, 1304, 1269, 1204, 1165, 1094, 1031, 1012 | Colorless needle crystal |

By using amino-alcohols prepared from the respective aldehydes and propargylamines in the same manner as in the method of Example 10, ynone compounds were prepared in the same manner as in Example 14. By using the obtained ynone compounds and using sodium benzenesulfinate, the compounds of Examples 24 to 28 were prepared in the same manner as in the method of Example 15. In the following, the structures of the used ynone compounds and the desired compounds and the physical properties and yields of the desired compounds are shown.

| Example No. | Structural formula | ¹H-NMR (250MHz)CDCl₃ δppm | IRcm⁻¹ | Yield (%) |
|---|---|---|---|---|
| 24 | Ynone compound | 1.21–1.50(m, 2H), 1.53(s, 6H), 1.60–1.78(m, 4H), 2.58–2.80(m, 4H), 6.08(s, 2H), 6.89(d, J=8.2Hz, 1H), 7.57(d, J=1.7Hz, 1H), 7.82(dd, J=8.2Hz, 1.7Hz, 1H) | (kBr) 2993, 2978, 2926, 2852, 2208, 1630, 1602, 1495, 1439, 1367, 1269, 925, 875, 860, 812, 719, 697, 613 Pale yellow crystal m.p. 97–97.5° C. | 74 |
| | Desired compound | 1.29(s, 6H), 1.30–1.42(m, 6H), 2.26–2.37(m, 4H), 6.06(s, 2H), 6.90(d, J=8.1Hz, 1H), 7.44–7.50(m, 5H), 7.74(s, 1H), 8.08(dd, J=7.7, 1.4Hz, 1H), | (kBr) 3449, 2919, 2811, 1657, 1602, 1503, 1485, 1447, 1304, 1258, 1146, 1111, 1034, 748 Colorless powder m.p. 138–139° C. | |
| 25 | Ynone compound | 1.40–1.50(m, 2H), 1.53(s, 6H), 1.60–1.78(m, 4H), 2.63–2.70(m, 4H), 3.96(s, 3H), 6.10(s, 2H), 7.36(d, J=1.5Hz, 1H), 7.48(d, J=1.5Hz, 1H) | (kBr) 2970, 2926, 2199, 1622, 1504, 1327, 1230, 1170, 1101, 1033, 966, 914, 864, 738, 470 Colorless crystal m.p. 69–72° C. | 42 |
| | Desired compound | 1.28(s, 6H), 1.33–1.43(m, 6H), 2.26–2.38(m, 4H), 3.96(s, 3H), 7.30(d, J=1.4Hz, 1H), 7.52–7.60(m, 3H), 7.74(s, 1H), 8.08(dd, J=7.7, 1.5Hz, 1H), | (kBr) 3426, 2932, 1663, 1628, 1508, 1453, 1433, 1370, 1308, 1146, 1105, 1032, 745 Colorless powder m.p. 157–159° C. | |
| 26 | Ynone compound | 1.42(s, 6H), 1.43–1.55(m, 2H), 1.58(ddd, J=10.7, 5.5, 5.4Hz, 4H), 2.53–2.57(m, 4H), 6.20(s, 2H), 7.10(s, 1H), 7.37(s, 1H) | (kBr) 3065, 2935, 2810, 2155, 1649, 1612, 1504, 1489, 1381, 1359, 1280, 1246, 1145, 1084, 1032, 922, 860, 756, 432, Pale yellow crystal m.p. 127–127.5° C. | 34 |
| | Desired compound | 1.20(s, 6H), 1.29–1.36(m, 6H), 2.22–2.32(m, 4H), 6.17(s, 2H), 7.38(s, 1H), 7.45(s, 1H), 7.52–7.65(m, 3H), 7.82(s, 1H), 8.08(dd, J=7.8, 1.9Hz, 1H), | (kBr) 3383, 2980, 2941, 1703, 1603, 1526, 1499, 1483, 1337, 1312, 1269, 1150, 1032 Yellow plate crystal m.p. 139–140° C. | |
| 27 | Ynone compound | 1.21–1.35(m, 2H), 1.54(s, 6H), 1.59–1.68(m, 3H), 2.19–2.36(m, 2H), 3.10–3.20(m, 2H), 3.95(s, 3H), 3.97 (s, 3H), 6.94(d, J=8.4Hz, 1H), 7.64 (d, J=1.9Hz, 1H), 7.86(dd, J=8.4, 1.9Hz, 1H) | (film) 2924, 2870, 2203, 1641, 1591, 1514, 1462, 1417, 1325, 1344, 1271, 1192, 1132, 1068, 1024, 968, 879, 815, 763 Pale yellow oily state | 38 |
| | Desired compound | | | |

| Example No. | Structural formula | $^1$H-NMR (250MHz)CDCl$_3$ δppm | IRcm$^{-1}$ | Yield (%) |
|---|---|---|---|---|
| | 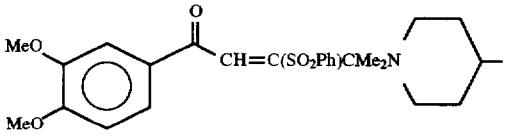 | 0.82(d, J=6.5Hz, 1H), 0.86–0.99 (m, 1H), 1.22–1.29(m, 2H), 1.30(s, 6H), 1.49–1.56(m, 2H), 1.96(t, J=10.0Hz, 2H), 2.70–2.80 (m, 2H), 3.95(s, 6H), 6.95(d, J=8.3 Hz, 1H), 7.48–7.60(m, 5H), 7.74(s, 1H), 8.09(dd, J=7.6, 1.5Hz, 1H) | (kBr) 3428, 2943, 1655, 1586, 1514, 1468, 1451, 1420, 1304, 1275, 1170, 1144, 1015, 748 Colorless powder m.p. 184–186° C. | |
| 28 | Ynone compound 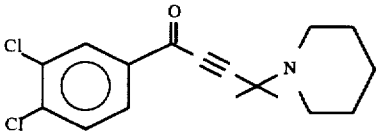 | 1.21–1.50(m, 2H), 1.53(s, 6H), 1.60–1.78(m, 4H), 2.58–2.80(m, 4H), 6.08(s, 2H), 6.89(d, J=8.2Hz, 1H), 7.57(d, J=1.7Hz, 1H), 7.82(dd, J=8.2, 1.7Hz, 1H) | (film) 2934, 2804, 2748, 2363, 2206, 1655, 1583, 1556, 1464, 1383, 1233, 1176, 1107, 1059, 966 912, 839, 742, 723 Pale yellow oily state | 29 |
| | Desired compound 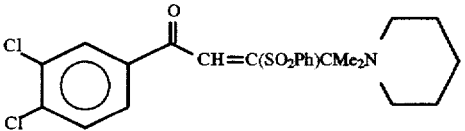 | 0.96–1.42(m, 12H), 2.10–2.18(m, 2H), 2.28–2.40(m, 2H), 7.55–7.74 (m, 6H), 7.95(dd, J=6.8, 1.8Hz, 2H), 8.02(dd, J=7.6, 1.1Hz, 1H) | (neat) 2936, 2855, 1674, 1584, 1559, 1447, 1385, 1308, 1146, 1032, 954, 833, 756 Pale yellow oily state | |

EXAMPLE 29

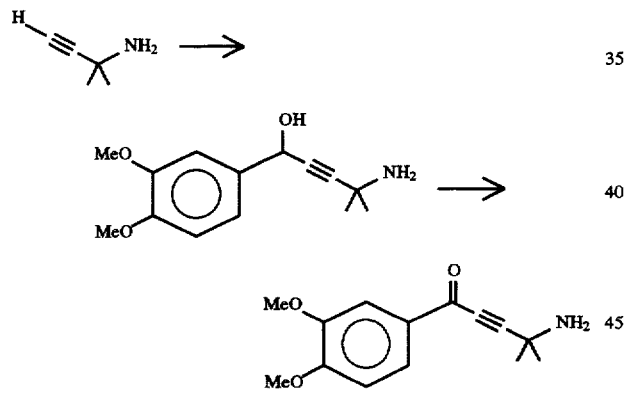

Molecular sieve 4A (10 g) was added to a tetrahydrofuran solution (50 ml) of 3-amino-3-methyl-1-butyne (5.0 g, 90% in H$_2$O, 54 mmol), and the mixture was stirred under nitrogen atmosphere for 30 minutes. Under nitrogen atmosphere, the molecular sieve was removed by filtration, and the filtrate was cooled by a dry ice-ethanol bath. To this filtrate was added dropwise a 1.63M n-butyl lithium hexane solution (33.0 ml, 54.0 mmol) over 2 hours. After the temperature of the reaction mixture was slowly raised to 0° C., the mixture was cooled again by a dry ice-ethanol bath, and veratraldehyde (8.97 g, 54.0 mmol) was added thereto. After the temperature of the reaction mixture was raised to room temperature, the mixture was cooled to 0° C., and water was added thereto to terminate the reaction. After the solvent was removed by evaporation under reduced pressure, water was added to the residue, and the product was extracted with dichloromethane (70 ml×2). The extract was dried (anhydrous sodium sulfate) and concentrated, and the obtained oily substance was purified by silica gel column chromatography (developing solution: chloroform/methanol=50/3) to give amino-alcohol (7.65 g, 57%) which was an adduct.

Amino-alcohol compound $^1$H NMR (CDCl$_3$, 250 MHz) δ ppm: 1.44 (s, 6H), 198 (brs, 3H), 3.89 and 3.90 (2s, 6H), 5.41 (s, 1H), 6.86 (d, J=8.7Hz, 1H), 7.03 to 7.10 (m, 2H). m.p. 85° to 87° C., pale yellow crystal At room temperature, to a dichloromethane solution (50 ml) of the above-mentioned amino-alcohol (1.65 g, 6.59 mmol) was added active manganese dioxide (10.2 g) 10 times each in an amount divided into 10. After 2 minutes, the reaction mixture was filtered with celite, and the residue was washed with dichloromethane (20 ml). The filtrate was concentrated to give an ynone compound (1.39 g, 85%).

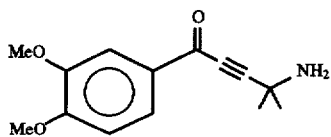

$^1$H NMR (250 MHz, CDCl$_3$) δ ppm: 1.54 (s, 6H), 1.78 (brs, 2H), 3.95 (s, 3H), 3.97 (s, 3H), 6.94 (d, J=8.4Hz, 1H), 7.60 (d, J=2.0Hz, 1H), 7.81 (dd, J=8.3, 1.9Hz, 1H). Pale yellow oily state

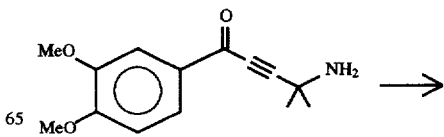

-continued

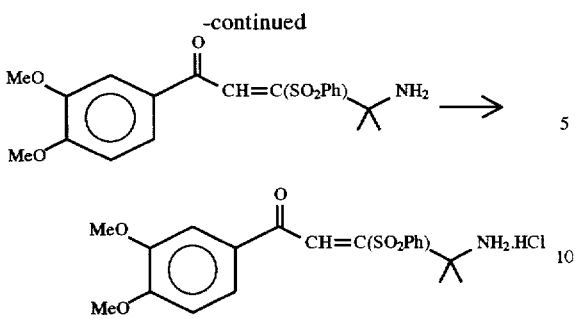

By using the above aminoynone compound (200 mg, 0.82 mmol) and sodium benzenesulfinate (160 mg, 0.82 mmol), a vinyl sulfone compound (210 mg, 66%) was obtained in the same manner as in Example 20. This compound was dissolved in a mixed solvent of diethyl ether (60 ml) and ethyl acetate (20 ml), and the solution was stirred under nitrogen atmosphere on an ice bath. A 4N hydrochloric acid-ethyl acetate solution (0.3 ml) was added dropwise thereto, and the mixture was stirred at the same temperature for 10 minutes. The produced precipitates were collected by filtration, dried and suspended in ethyl acetate-diethyl ether (1/5). After stirring for 10 minutes, the precipitates were collected by filtration to give hydrochloride of a desired vinyl sulfone compound (200 mg, 91%).

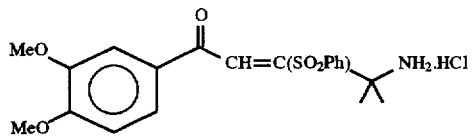

$^1$H NMR (250 MHz, CDCl$_3$) δ ppm: 1.90 (s, 6H), 3.86 (s, 3H), 3.94 (s, 3H), 6.95 (d, J=8.5Hz, 1H), 7.41 to 7.60 (m, 5H), 8.02 (dd, J=8.3, 1.9Hz, 1H), 8.12 (dd, J=7.9, 1.0Hz, 2H), 9.19 (brs, 2H). IR (KBr) cm$^{-1}$: 3407, 3227, 2841, 2037, 1658, 1588, 1514, 1443, 1422, 1310, 1269, 1173, 1146, 1080, 1019, 752, 632. m.p. 149° to 151° C., yellow columnar crystal

EXAMPLE 30

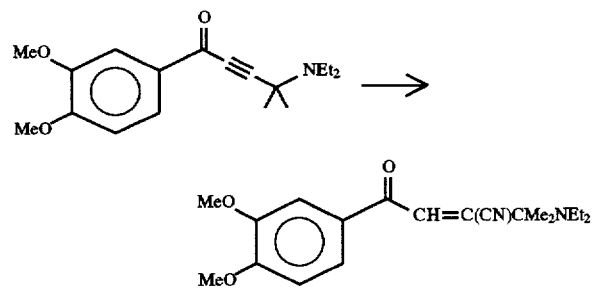

The ynone compound (200 mg, 0.66 mmol) obtained in Example 19 was dissolved in 10 ml of toluene, and while stirring the solution under nitrogen atmosphere on an ice water bath, a toluene solution (1.3 ml, 1.32 mmol) of 1.0M diethyl aluminum cyanide was added dropwise thereto. The temperature of the mixture was raised to room temperature, and stirring was continued. After disappearance of the starting materials was confirmed, a 2N sodium hydroxide aqueous solution was added to the mixture, and the mixture was extracted twice with each 20 ml of toluene. The residue obtained after the organic layer was washed with water, dried (Na$_2$SO$_4$) and concentrated was applied to silica gel column chromatography (chloroform:methanol=30:1) to give a cyano compound (20 mg, 9%) from a desired fraction.

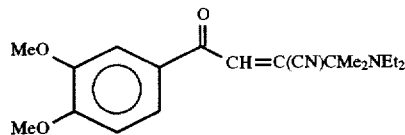

$^1$H NMR (250 MHz, CDCl$_3$) δ ppm: 1.11 (t, J=7.2Hz, 6H), 1.41 (s, 6H), 2.63 (q, J=7.1Hz, 4H), 3.94 (s, 3H), 3.97 (s, 3H), 6.92 (d, J=8.4Hz, 1H), 7.51 (dd, J=8.3, 1.9Hz, 1H), 7.60 (s, 2H). m.p. 82° to 83° C., orange-tinted yellow plate crystal IR (KBr) cm$^{-1}$: 3424, 2969, 2824, 2214, 1660, 1597, 1582, 1518, 1426, 1273, 1157, 1020.

EXAMPLE 31

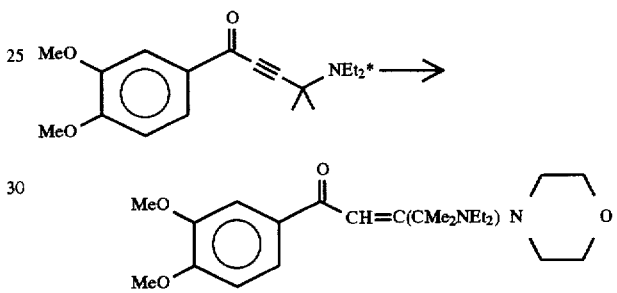

The ynone compound (500 mg, 1.65 mmol) obtained in Example 19 and morpholine (150 mg, 1.65 mmol) were dissolved in 7 ml of methanol, and the mixture was stirred at room temperature overnight. After completion of the reaction, the residue obtained by concentrating the solvent under reduced pressure was applied to silica gel column chromatography (n-hexane:ethyl acetate=2:1) to give a desired compound (410 mg, 64%) from a desired fraction.

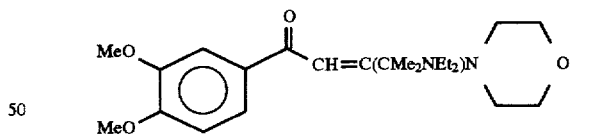

$^1$H NMR (CDCl$_3$, 250 MHz) δ ppm: 1.06 (t, J=7.1Hz, 6H), 1.39 (s, 6H), 2.57 (q, J=7.2Hz, 4H), 3.76 to 3.82 (m, 8H), 3.92 (s, 3H), 3.94 (s, 3H), 5.86 (s, 1H), 6.85 (d, J=8.3Hz, 1H), 7.44 (dd, J=8.3, 1.9Hz, 1H), 7.53 (d, J=1.9Hz, 1H). m.p. yellow oily substance IR (neat) cm$^{-1}$: 3422, 2994, 2951, 2838, 2363, 1844, 1615, 1580, 1505, 1462, 1410, 1390, 1362, 1260, 1204, 1154, 1125, 1026.

EXAMPLE 32

In the same manner as in Example 31, from the ynone compound obtained in Example 19 and monomethylamine, a vinylamine compound (yield: 95%)

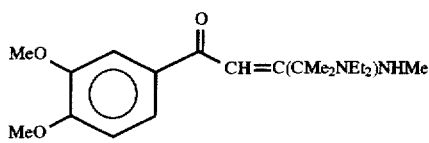

was obtained.

¹H NMR (CDCl₃, 250 MHz) δ ppm: 1.09 (t, 7.1Hz, 6H), 1.38 (s, 6H), 2.57 (q, J=7.1Hz, 4H), 3.52 (d, J=5.2Hz, 3H), 3.92 (s, 3H), 3.94 (s, 3H), 5.77 (s, 1H), 6.85 (d, J=8.4Hz, 1H), 7.42 (dd, J=8.3, 1.7Hz, 1H), 7.52 (d, J=1.8Hz, 1H). Colorless oily state IR (neat) cm⁻¹: 2971, 2836, 2045, 1738, 1609, 1557, 1507, 1464, 1391, 1300, 1211, 1175, 1144, 1026, 774.

EXAMPLE 33

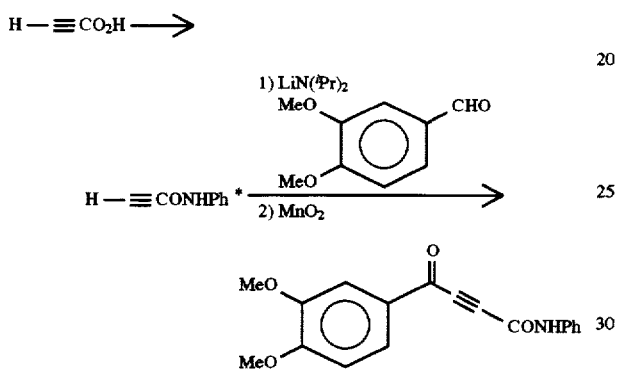

A tetrahydrofuran solution (100 ml) of propiolic acid (5.64 g, 80 mmol) was stirred on an ice bath, and triethylamine (13.4 ml, 96 mmol), aniline (8.0 ml, 88 mmol) and phosphorus oxychloride (8.2 ml, 88 mmol) were added thereto. The mixture was stirred at room temperature overnight, and to the reaction mixture was added water under ice cooling. Under reduced pressure, the solvent was removed by evaporation, and the residue was extracted with ethyl acetate (50 ml×2). After the extract was concentrated, the residue was purified by silica gel column chromatography (developing solution: chloroform/ethyl acetate=2/1) to obtain an anilide compound (5.58 g, yield: 48%). Under nitrogen atmosphere, a tetrahydrofuran solution (40 ml) of the anilide compound (1.60 g, 11.0 mmol) was cooled to −70° C., and while stirring the solution, a 2M lithium diisopropyl amide cyclohexane solution (11.6 ml, 23.1 mmol) was slowly added dropwise thereto. After the mixture was stirred for 1 hour, 3,4-dimethoxybenzaldehyde (1.83 g, 11.0 mmol) was added to thereto. The temperature of the reaction mixture was raised to room temperature over 1 hour, the mixture was subsequently cooled to 0° C., and then water (10 ml) was added thereto to terminate the reaction. After the solvent was removed by evaporation under reduced pressure, water (30 ml) was added to the residue, and the product was extracted with ethyl acetate (50 ml). After the extract was dried (anhydrous sodium sulfate) and concentrated, the residue obtained was purified by silica gel column chromatography (developing solution: chloroform/ethyl acetate=4/1) to give an alcohol compound (1.22 g, 36%) which was an adduct. This alcohol compound (1.20 g, 3.9 mmol) was subjected to an oxidation reaction by the same method as in Example 14, and the obtained crude product was applied to silica gel column chromatography (developing solution=n-hexane/chloroform/ethyl acetate=1/1/1) and then rinsed with ether-hexane and collected by filtration to give the desired above-mentioned ketone compound (630 mg, yield: 53%).

¹H NMR (250 MHz, CDCl₃) δ ppm: 3.93 and 3.97 (2s, 6H), 6.75 (d, J=8.5Hz, 1H), 7.19 (t, J=7.6Hz, 1H), 7.37 (m, 12H), 7.54 (d, J=1.8Hz, 1H), 7.60 (d, J=8.2Hz, 2H), 7.83 (dd, J=1.9, 8.5Hz, 1H), 8.36 (brs, 1H). Shape: pale orange powder m.p. 140° to 142° C. IR (KBr) cm⁻¹: 3324, 1680, 1630, 1599, 1584, 1545, 1510, 1462, 1442, 1420, 1321, 1271, 1171, 1144, 1020, 874, 760.

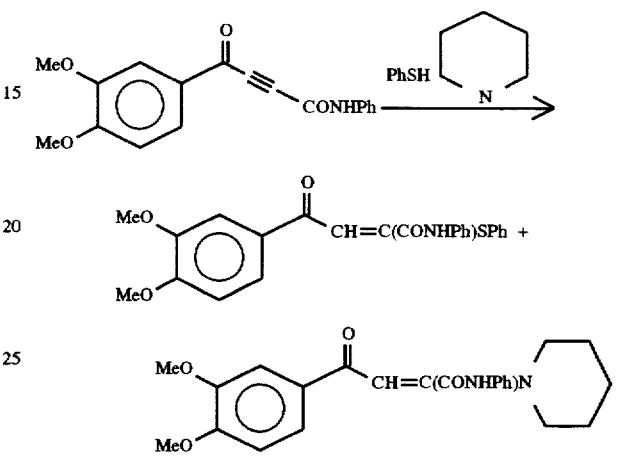

The above ketone compound (200 mg, 0.65 mmol) was dissolved in 5 ml of dichloromethane, 70 ml (0.65 mmol) of thiophenol and one drop of piperidine were added dropwise thereto, and the mixture was stirred at room temperature overnight. The residue obtained after the solvent was concentrated was applied to silica gel column chromatography (n-hexane:ethyl acetate=4:1) to give a sulfide compound (10 mg, 4%) and an amine compound (30 mg, 12%) from desired fractions.

Sulfide compound

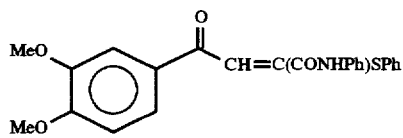

¹H NMR (250 MHz, CDCl₃) δ ppm: 3.95 (s, 3H), 3.97 (s, 3H), 6.92 (d, J=8.2Hz, 1H), 7.06 to 7.32 (m, 8H), 7.47 (d, J=7.0Hz, 2H), 7.58 (s, 1H), 7.68 (d, J=9.8Hz, 1H), 7.83 (brs, 1H), 7.89 (s, 1H).

Amine compound

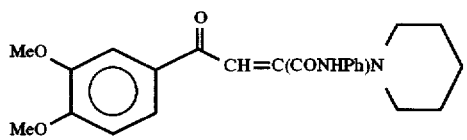

¹H NMR (250 MHz, CDCl₃) δ ppm: 1.71 (brs, 6H), 4.33 (brs, 4H), 3.89 (s, 3H), 3.92 (s, 3H), 5.90 (s, 1H), 6.84 (d, J=8.3Hz, 1H), 7.13 (t, J=7.4Hz, 1H), 7.35 (t, J=8.1Hz, 2H), 7.47 to 7.54 (m, 3H), 7.65 (d, J=8.3Hz, 2H). IR (KBr) cm⁻¹: 3345, 2938, 1686, 1599, 1545, 1508, 1439, 1254, 1165, 1022, 870, 758. m.p. 196° to 198° C., colorless needle crystal

EXAMPLE 34

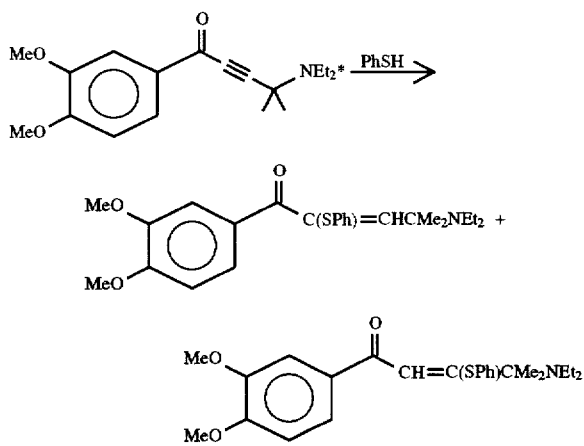

The ynone compound (500 mg, 1.65 mmol) obtained in Example 19, thiophenol (180 mg, 1.65 mmol) and a catalytic amount of piperidine were dissolved in 5 ml of ether, and the mixture was stirred under nitrogen atmosphere at room temperature for 7 hours. After disappearance of the starting materials was confirmed, the residue given by concentrating the solvent was applied to silica gel column chromatography (n-hexane:ethyl acetate=3:1) to obtain an α-sulfide compound (430 mg, 63%) and a β-sulfide compound (170 mg, 25%) from desired fractions.

α-Sulfide compound

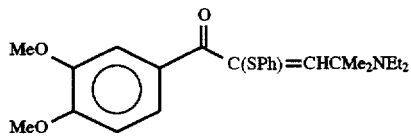

$^1$H NMR (250 MHz, CDCl$_3$) δ ppm: 1.13 (t, J=7.1Hz, 6H), 1.48 (s, 6H), 2.68 (q, J=7.1Hz, 4H), 3.82 (s, 3H), 3.93 (s, 3H), 6.66 (s, 1H), 6.78 (d, J=8.5Hz, 1H), 7.01 (s, 6H), 7.34 (d, J=8.5Hz, 1H).

β-Sulfide compound

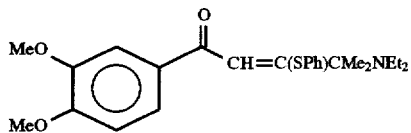

$^1$H NMR (250 MHz, CDCl$_3$) δ ppm: 1.01 (t, J=7.1Hz, 6H), 1.44 (s, 6H), 2.56 (q, J=7.1Hz, 4H), 3.89 (s, 3H), 3.91 (s, 3H), 5.69 (s, 1H), 6.82 (d, J=8.2Hz, 1H), 7.33 to 7.38 (m, 5H), 7.57 (dd, J=8.1, 1.7Hz, 2H).

EXAMPLE 35

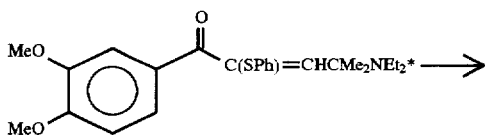

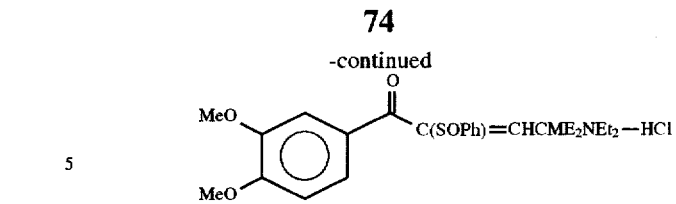

The α-sulfide compound (100 mg, 0.24 mmol) obtained in Example 34 was dissolved in 10 ml of chloroform, and while stirring the solution on an ice water bath, 80 mg of mCPBA (purity: 55%) was added thereto. The temperature of the mixture was raised to room temperature, and stirring was continued for 2 hours. After disappearance of the starting materials were confirmed, a saturated sodium hydrogen carbonate aqueous solution (0.24 mmol) was added to the mixture, and the mixture was extracted twice with each 20 ml of chloroform. The residue obtained by washing the organic layer with water, drying it (Na$_2$SO$_4$) and concentrating it was applied to silica gel chromatography (n-hexane:ethyl acetate=2:1) to give a sulfoxide compound (50 mg, 48%).

40 mg of the compound obtained here was dissolved in 10 ml of diethyl ether, a 4N-hydrochloric acid ethyl acetate solution (0.2 ml) was added dropwise thereto under nitrogen atmosphere on an ice bath, and the mixture was stirred at the same temperature for 10 minutes. The produced precipitates were collected by filtration, dried and suspended in ethyl acetate-diethyl ether (1/5). After stirring for 10 minutes, the precipitates were collected by filtration to give hydrochloride of a desired sulfoxide (30 mg, 69%).

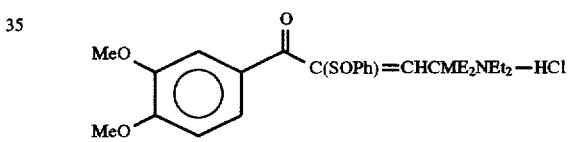

$^1$H NMR (250 MHz, CDCl$_3$) δ ppm: 1.21 to 1.76 (m, 12H), 3.23 to 3.86 (m, 4H), 4.02 (s, 3H), 4.06 (s, 3H), 7.05 (d, J=8.5Hz, 1H), 7.57 to 7.75 (m, 6H), 8.01 (dd, J=8.5, 2.0Hz, 1H), 8.43 (s, 1H), 10.49 (brs, 1H). m.p. yellow oily state IR (KBr) cm$^{-1}$: 3409, 3003, 1649, 1582, 1512, 1424, 1304, 1265, 1173, 1152, 1020, 984, 754.

EXAMPLE 36

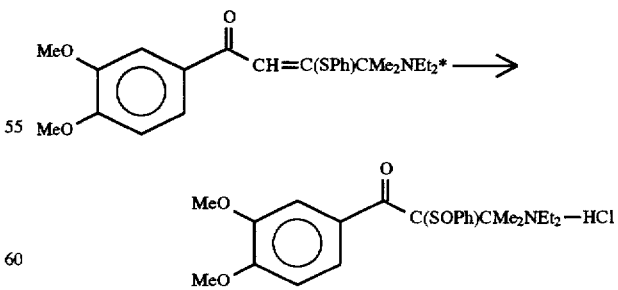

From the β-sulfide compound (80 mg, 0.19 mmol) obtained in Example 34, hydrochloride of sulfoxide (60 mg, overall yield: 68%) was obtained by the same method as in Example 35.

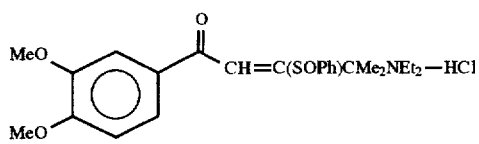

$CH=C(SOPh)CMe_2NEt_2 \cdot HCl$ $^1$H NMR (250 MHz, CDCl$_3$) δ ppm: 1.51 to 1.84 (m, 12H), 2.96 to 3.22 (m, 2H), 3.42 to 3.54 (m, 1H), 3.80 to 3.98 (m, 1H), 3.97 (s, 3H), 4.00 (s, 3H), 7.08 (d, J=8.4Hz, 1H), 7.52 to 7.61 (m, 3H), 7.76 (s, 1H), 7.87 (dd, J=8.2Hz, 2H), 8.39 (d, J=8.4Hz, 1H), 9.62 (s, 1H), 11.10 (brs, 1H). m.p. 110° to 112° C., colorless powder IR (KBr) cm$^{-1}$: 3407, 2986, 1628, 1593, 1572, 1514, 1444, 1422, 1275, 1219, 1154, 1076, 1015, 872, 768.

Test example

In order to evaluate the tyrosine kinase inhibiting activity and the cancer cell growth inhibiting activity of the compound of the present invention, tests were carried out in a partially purified human EGF (epithelial cell growth factor) receptor tyrosine kinase activity measuring system and a cell culture system using human cancerous cells.

(Tyrosine kinase inhibiting activity)
(Measurement method)

The tyrosine kinase inhibiting activity was measured by using an EGF receptor which was partially purified from an A431 cell line derived from human squamous cell carcinoma and by improving the tyrosine kinase activity measurement method described in Linda J. Pike et al., Proceedings of the National Academy of Sciences of the U.S.A. 79, 1443 (1982).

The detailed method is as described below.

A431 cells were cultured in a Dulbecco modified Eagle's medium (DMEM) containing 10% fetal calf serum (FCS), at 37° C. under 5% carbonic acid gas. The cells were homogenized in a solution containing 10 mM N-2-hydroxyethylpiperazino-N'-2-ethanesulfonic acid (Hepes) buffer (pH 7.4), 0.25M saccharose and 0.1 mM EDTA and then centrifuged at 3000 g for 5 minutes. Further, a supernatant thereof was centrifuged at 10000× g for 30 minutes to obtain an A431 cell membrane fraction, and this fraction was provided for measurement as a partially purified EGF receptor which was an enzyme source.

To a reaction mixture of the above-mentioned A431 cell membrane fraction (10 to 15 µg), a 30 mM Hepes buffer (pH 7.7), 2 mM MnCl$_2$, 50 µM Na$_3$VO$_4$ and a sample dissolved in dimethylsulfoxide (DMSO) (final concentration: 1% DMSO) was added 100 ng of EGF, and then 75 µg of a synthetic substrate RR-SRC peptide (a peptide described in Sequence No. 1) and 10 µM gamma-$^{32}$P-adenosine triphosphoric acid (37 to 42 KBq) were added thereto to start a reaction.

The volume at that time was 60 µl.

The reaction was carried out in ice for 30 minutes, and the reaction was terminated by adding 6 µl of 10 mg/ml bovine serum albumin and 25 µl of 20% trichloroacetic acid. The reaction mixture was left to stand in ice for 30 minutes.

Next, after the mixture was centrifuged at 5000× g for 2 minutes, 40 µl of the supernatant was sampled and adsorbed to P81 phosphocellulose paper.

This was dipped in a 30% acetic acid solution for 15 minutes to fix, washed by dipping in a 15% acetic acid solution for 15 minutes (washing was repeated four times) and measured the count of $^{32}$P attached to P81 phosphocellulose paper by a liquid scintillation counter, and this value was defined as A.

At the same time, the counts of a reaction in which the sample tested was not added and a reaction in which both the sample and EGF were not added were measured and were defined as B and C, respectively.

The tyrosine kinase inhibiting rate is determined by the following formula.

Inhibiting rate (%)=100−{(B−A)/(B−C)}×100

From the inhibiting rate obtained by changing the addition concentration of the sample, an IC$_{50}$ value (50% inhibiting concentration) was calculated.

(Cancer cell growth inhibiting activity)
(Measurement method)

KB cells of human rhinopharyngeal cancer retain EGF receptor on cellular surfaces thereof excessively.

By using these KB cells, investigation of the effect of a sample on growth of cultured cancer cells was carried out by the following method.

2.5×10$^3$ cells/well of KB cells were sowed on a 96 well dish and cultured in a DMEM:F12 (1:1) medium containing 10% FCS, 50 U/ml penicillin and 50 µg/ml of streptomycin, under conditions of 37° C. and 5% carbonic acid gas for 1 day. Thereafter, a sample dissolved in DMSO was added to the medium (DMSO final concentration: <0.1%) and cultured under the above conditions for 3 days. The sample and the medium were replaced every 24 hours.

The count of the number of living cells was determined by calorimetric quantitation at two wavelengths of 540 nm and 660 nm using a MTT reagent by referring to the measurement method described in Michael C. Alley et al, Cancer Research 48, 589 (1988), and the value was defined as a.

At the same time, the count of the number of living cells when the sample was not added was also measured, and the value was defined as b.

The cell growth inhibiting rate was determined by the following formula.

Inhibiting rate (%)=(b−a)/b×100

From the inhibiting rate obtained by changing the addition concentration of the sample, an IC$_{50}$ value (50% inhibiting concentration) was calculated.

The above results are shown in Table-2.

TABLE 2

| Compound (No.) | Tyrosine kinase inhibiting activity (IC$_{50}$, µM) | Cancer cell growth inhibiting activity (IC$_{50}$, µM) |
|---|---|---|
| 5 | 0.34 | 0.62 |
| 26 | 0.86 | 1.9 |
| 29 | 9.4 | 3.9 |
| 97 | 8.2 | 2.6 |
| 335 | 27.9 | 3.1 |
| 278 | 1.7 | 0.95 |
| 293 | 1.1 | 0.23 |
| 350 | 1.4 | 0.57 |
| 352 | 0.47 | 0.63 |
| 349 | 5.8 | 2.0 |
| 290 | 5.0 | 0.83 |
| 327 | 27.3 | 5.0 |
| 253 | 38 | 0.42 |

Utilizability in Industry

The benzoylethylene derivative of the present invention has potent tyrosine kinase inhibiting activity and cancer cell growth inhibiting activity, and the tyrosine kinase inhibitor of the present invention is useful as a carcinostatic agent.

We claim:

1. A benzoylethylene derivative represented by the following formula (I):

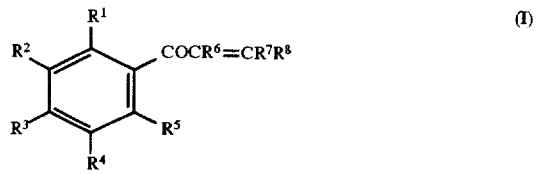

wherein, in the above formula (I), $R^1$ to $R^5$ each independently represent (1) a hydrogen atom, (2) —$OR^9$, wherein $R^9$ represents a hydrogen atom or a $C_1$–$C_5$ alkyl group which may be substituted by a halogen atom or a phenyl group, (3) a halogen atom, (4) a $C_1$–$C_5$ alkyl group which may be substituted by a halogen atom, (5) —$NR^{10}R^{11}$ (wherein $R^{10}$ and $R^{11}$ each independently represent a hydrogen atom, a phenyl group, a $C_1$–$C_5$ alkyl group which may be substituted by a phenyl group, a benzoyl group or an acetyl group), (6) —$SO_pR^2$ (wherein p represents 0, 1 or 2, and $R^{12}$ represents a $C_1$–$C_5$ alkyl group or a phenyl group), (7) a cyano group or (8) a nitro group, or represent a $C_1$–$C_3$ alkyl group oxyalkylene group having 1 or 2 oxygen atoms by combining the adjacent substituents, $R^6$ and $R^7$ each represent one of (1) a hydrogen atom, (2) a cyano group, (3) a halogen atom, (4) a $C_1$–$C_5$ alkyl group which may be substituted by a halogen atom, (5) —$NR^{13}R^{14}$ (wherein $R^{13}$ and $R^{14}$ each independently represent a hydrogen atom or a $C_1$–$C_5$ alkyl group, or are combined together to form a $C_3$–$C_6$ alkylene group which may be intervened by —O—) or (6) —$SO_qR^{15}$ (wherein q represents 0, 1 or 2, and $R^{15}$ represents a $C_1$–$C_5$ alkyl group which may be substituted by a halogen atom, a thienyl group or a phenyl group which may be substituted by a halogen atom, a $C_1$–$C_5$ alkyl group, a cyano group, a nitro group or a $C_1$–$C_5$ alkoxy group) provided that $R^6$ and $R^7$ are not both hydrogen, $R^8$ represents —$CR^{22}R^{23}X$, wherein $R^{22}$ and $R^{23}$ each independently represent a hydrogen atom or a $C_1$–$C_5$ alkyl group, or are combined together to represent a $C_3$–$C_6$ alkylene group which may be substituted by a $C_1$–$C_5$ alkyl group, and X represents —$NR^{24}R^{25}$, wherein $R^{24}$ and $R^{25}$ each independently represent (a) a hydrogen atom, (b) a phenyl group which may be substituted by a halogen atom or a $C_1$–$C_5$ alkyl group, (c) a $C_1$–$C_5$ alkyl group which may be substituted by a phenyl group or a $C_1$–$C_5$ alkylamino group, (d) a $C_3$–$C_8$ cycloalkyl group or (e) —$COR^{26}$ (wherein $R^{26}$ represents a $C_1$–$C_5$ alkyl group, a phenyl group or a $C_1$–$C_5$ alkoxy group which may be substituted by a phenyl group), or are combined together to represent a $C_3$–$C_6$ alkylene group which may be intervened by —O— or —$NR^{27}$— (wherein $R^{27}$ represents a hydrogen atom or a $C_1$–$C_5$ alkyl group), or a $C_3$–$C_6$ alkylene group which may be substituted by a $C_1$–$C_5$ alkyl group, or a salt thereof.

2. The compound according to claim 1, wherein $R^7$ is a hydrogen atom, a cyano group, a $C_1$–$C_5$ alkyl group or —$SO_qR^{15}$ (wherein q represents 0, 1 or 2, and $R^{15}$ represents a $C_1$–$C_5$ alkyl group which may be substituted by a halogen atom, a thienyl group or a phenyl group which may be substituted by a halogen atom, a $C_1$–$C_5$ alkyl group, a cyano group, a nitro group or a $C_1$–$C_5$ alkoxy group), and $R^8$ is —$CR^{22}R^{23}X$, wherein $R^{22}$ and $R^{23}$ each independently represent a hydrogen atom or a $C_1$–$C_5$ alkyl group, or are combined together to represent a $C_3$–$C_6$ alkylene group which may be substituted by a $C_1$–$C_5$ alkyl group, and X represents —$NR^{24}R^{25}$, wherein $R^{24}$ and $R^{25}$ each independently represent (a) a hydrogen atom, (b) a phenyl group which may be substituted by a halogen atom or a $C_1$–$C_5$ alkyl group, (c) a $C_1$–$C_5$ alkyl group which may be substituted by a phenyl group or a $C_1$–$C_5$ alkylamino group, (d) a $C_3$–$C_8$ cycloalkyl group or (e) —$COR^{26}$ (wherein $R^{26}$ represents a $C_1$–$C_5$ alkyl group, a phenyl group or a $C_1$–$C_5$ alkoxy group which may be substituted by a phenyl group), or are combined together to represent a $C_3$–$C_6$ alkylene group which may be intervened by —O— or —$NR^{27}$— (wherein $R^{27}$ represents a hydrogen atom or a $C_1$–$C_5$ alkyl group), or a $C_3$–$C_6$ alkylene group which may be substituted by a $C_1$–$C_5$ alkyl group.

3. The compound according to claim 1, wherein $R^1$ and $R^5$ are hydrogen atoms, $R^2$, $R^3$ and $R^4$ each independently are a hydrogen atom or —$OR^{9'}$ (wherein $R^{9'}$ represents a $C_1$–$C_5$ alkyl group), or $R^2$ and $R^3$ are combined to be $C_1-C_3$ oxyalkylene having 1 or 2 oxygen atoms, $R^6$ is a hydrogen atom or a $C_1-C_5$ alkyl group, $R^7$ is a hydrogen atom provided that $R^6$ is not hydrogen atom, a cyano group, a $C_1-C_5$ alkyl group or $-SO_{q'}R^{15'}$ (wherein q' represents 2, and $R^{15'}$ represents a thienyl group or a phenyl group which may be substituted by a $C_1-C_5$ alkyl group or a nitro group), and $R^8$ is $-CR^{22'}R^{23'}X'$ (wherein $R^{22'}$ and $R^{23'}$ each independently represent a hydrogen atom or a $C_1-C_5$ alkyl group, and X' represents $-NR^{24'}R^{25'}$ (wherein $R^{24'}$ and $R^{25'}$ each independently represent a $C_1-C_5$ alkyl group or are combined together to represent a $C_3-C_6$ alkylene group which may be substituted by a $C_1-C_5$ alkyl group).

4. The compound according to claim 1, wherein $R^1$, $R^4$ and $R^5$ are hydrogen atoms, $R^2$ and $R^3$ each independently are $-OR^{9'}$ (wherein $R^{9'}$ represents a $C_1-C_5$ alkyl group), $R^6$ is a hydrogen atom, $R^7$ is $-SO_{q'}R^{15''}$ (wherein q' represents 2, and $R^{15''}$ represents a phenyl group which may be substituted by a $C_1-C_5$ alkyl group or a nitro group), and $R^8$ is $-CR^{22''}R^{23''}X''$, wherein $R^{22''}$ and $R^{23''}$ each independently represent a $C_1-C_5$ alkyl group, and X'' represents $-NR^{24''}R^{25''}$ (wherein $R^{24''}$ and $R^{25''}$ each independently represent a $C_1-C_5$ alkyl group).

5. A benzoylethylene derivative represented by the following formula (I):

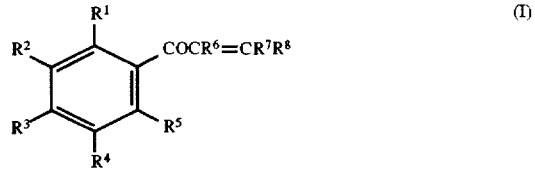

wherein $R^1$, $R^4$ and $R^5$ are hydrogen atoms, $R^2$ and $R^3$ are methoxy groups, $R^6$ is a hydrogen atom, $R^7$ is a phenylsulfonyl group, and $R^8$ is $-C(CH_3)_2N(C_2H_5)_2$.

6. A tyrosine kinase inhibitor which comprises the compound according to claim 1 as an active ingredient in a pharmaceutically acceptable carrier.

7. A tyrosine kinase inhibitor which comprises the compound according to claim 5 as an active ingredient, in a pharmaceutically acceptable carrier.

* * * * *